US012618847B2

(12) United States Patent
Trader et al.

(10) Patent No.: US 12,618,847 B2
(45) Date of Patent: May 5, 2026

(54) ACTIVITY-BASED PROBES WITH UNNATURAL AMINO ACIDS TO MONITOR PROTEASOME ACTIVITY

(71) Applicant: Purdue Research Foundation, West Lafayette, IN (US)

(72) Inventors: Darci J. Trader, West Lafayette, IN (US); Andres Salazar-Chaparro, West Lafayette, IN (US); Breanna Zerfas, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 860 days.

(21) Appl. No.: 17/905,921

(22) PCT Filed: Mar. 11, 2021

(86) PCT No.: PCT/US2021/021950
§ 371 (c)(1),
(2) Date: Sep. 8, 2022

(87) PCT Pub. No.: WO2021/183789
PCT Pub. Date: Sep. 16, 2021

(65) Prior Publication Data

US 2023/0108494 A1 Apr. 6, 2023

Related U.S. Application Data

(60) Provisional application No. 62/987,919, filed on Mar. 11, 2020.

(51) Int. Cl.
*A61K 38/00* (2006.01)
*C09B 11/08* (2006.01)
*C09K 11/06* (2006.01)
*G01N 21/64* (2006.01)
*G01N 33/50* (2006.01)
*G01N 33/58* (2006.01)

(52) U.S. Cl.
CPC ............ *G01N 33/582* (2013.01); *C09B 11/08* (2013.01); *C09K 11/06* (2013.01); *G01N 21/6428* (2013.01); *G01N 33/5011* (2013.01); *C09K 2211/1018* (2013.01)

(58) Field of Classification Search
CPC ....... C07D 493/10; C09B 11/08; C09K 11/06; C09K 2211/1018; G01N 21/6428; G01N 33/5011; G01N 33/582
See application file for complete search history.

(56) References Cited

U.S. PATENT DOCUMENTS

| | | | |
|---|---|---|---|
| 1,981,515 | A | 11/1934 | Kyrides |
| 2006/0021546 | A1 | 2/2006 | Wu et al. |
| 2012/0135443 | A1 | 5/2012 | Schultz |
| 2014/0349965 | A1 | 11/2014 | Anderson et al. |

FOREIGN PATENT DOCUMENTS

WO WO-2021183789 A1 9/2021

OTHER PUBLICATIONS

Zerfas et al. (J. Am. Chem. Soc. Mar. 20, 2019;141(13):5252-5260). Monitoring the Immunoproteasome in Live Cells Using an Activity-Based Peptide-Peptoid Hybrid Probe. (Year: 2019).*
Thibaudeau et al. (Pharmacol Rev 71:170-197, 2019). A Practical Review of Proteasome Pharmacology (Year: 2019).*
Bruin et al. (Doctoral Thesis, Jun. 1, 2016) (Year: 2016).*
"International Application Serial No. PCT/US2021/021950, International Search Report mailed Jul. 28, 2021", 4 pgs.
"International Application Serial No. PCT/US2021/021950, Invitation to Pay Additional Fees and Partial Search Report mailed May 24, 2021", 2 pgs.
"International Application Serial No. PCT/US2021/021950, Written Opinion mailed Jul. 28, 2021", 5 pgs.
"International Application Serial No. PCT US2021 021950, International Preliminary Report on Patentability mailed Sep. 22, 2022", 6 pgs.
Adams, J, "The Proteasome Structure, Function, and Role in the Cell", Cancer Treat. Rev. 29, [Online]. Retrieved from the Internet https doi. org 10.1016 S0305-73720300081-1, 2003, 7 pgs.
Adams, J, "Potential for Proteasome Inhibition in the Treatment of Cancer", Drug Discov. 8 7, [Online]. Retrieved from the Internet https doi.org 10.1016 S1359-64460302647-3, 2003, 9 pgs.
Adams, Julian, "Development of the Proteasome Inhibitor VelcadeTM Bortezomib", Cancer Invest. 2004, 22 2,, [Online]. Retrieved from the Internet URL https doi.org 10.1081 CNV-120030218, 2004, 4 pgs.
Almond, J. B., "The proteasome a novel target for cancer chemotherapy", Leukemia, 16, 2002, 11 pgs.
Checler, F, "Role of the Proteasome in Alzheimer's Disease", Biochim. Biophys. Acta BBA, Mol. Basis Dis, 133-138, [Online]. Retrieved from the Internet URL https doi.org 10.1016 S092544390000039-9., 2000, 6 pgs.
Chen, Ping, "Biogenesis, Structure and Function of the Yeast 20S Proteasome", The EMBO Journal vol. 14 No. 11, pp. 2620-2630, 1995, 11 pgs.
Chondrogianni, N, "Overexpression of Proteasome 5 Assembled Subunit Increases the Amount of Proteasome and Confers Ameliorated Response to Oxidative Stress and Higher Survival Rates", J. Biol. Chem. 280 12, [Online]. Retrieved from the Internet https doi.org 10.1074 jbc.M413007200, 2005, 11 pgs.
Coleman, R A, "Methods to Discover and Evaluate Proteasome Small Molecule Stimulators", Molecules 24 12, [Online]. Retrieved from the Internet https doi.org 10.3390 molecules24122341, 2019, 14 pgs.
Coleman, R A, "All About the Core A Therapeutic Strategy to Prevent Protein Accumulation with Proteasome Core Particle Stimulators", ACS Pharmacol. Transl. Sci. 1 2, [Online]. Retrieved from the Internet https doi.org 10.1021 acsptsci.8b00042, 2018, 3 pgs.

(Continued)

*Primary Examiner* — Lianko G Garyu
*Assistant Examiner* — Mercy H Sabila
(74) *Attorney, Agent, or Firm* — Schwegman Lundberg & Woessner, P.A.

(57) ABSTRACT

The disclosure relates to a compound of the formula (I) and the use of such compounds.

13 Claims, 8 Drawing Sheets

Specification includes a Sequence Listing.

(56) References Cited

OTHER PUBLICATIONS

Coleman, Rachel A, "Analysis of chain length, substitution patterns, and unsaturation of AM-404 derivatives as 20S proteasome stimulators", Bioorganic and Medicinal Chemistry Letters 29 3, pp. 420-423, [Online] Retrieved from the internethttps doi.org 10.1016 j.bmcl.2018.12.030, Dec. 19, 2018, 4 pgs.
Coux, O, "Structure and Functions of the 20S and 26S Proteasomes", Annu. Rev. Biochem. 1996, 65 1, [Online]. Retrieved from the Internet https doi.org 10.1146 annurev.bi.65.070196.004101, 1996, 47 pgs.
Cromm, Philipp M., "The Proteasome in Modern Drug Discovery Second Life of a Highly Valuable Drug Target", ACS Cent. Sci. 2017, 3 8, 830-838, 2017, 9 pgs.
Dasgupta, Sayani, "Proteasome Inhibitors Alter Levels of Intracellular Peptides in HEK293T and SH-SY5Y Cells", PLOS One, 97, e103604, [Online] Retrieved from the internethttps doi.org 10.1371 journal.pone.0103604, 2014.
Deger, J M, "The Interrelationship of Proteasome Impairment and Oligomeric Intermediates in Neurodegeneration", Aging Cell 14 5, [Online]. Retrieved from the Internet https doi.org 10.1111 acel. 12359, 2015, 10 pgs.
Dick, Tobias P, "Contribution of Proteasomal β-Subunits to the Cleavage of Peptide Substrates Analyzed with Yeast Mutants", The Journal of Biological Chemistry, vol. 273, No. 40, pp. 25637-25646, [Online] Retrieved from the internethttps doi.org 10.1074 jbc.273. 40.25637, Oct. 2, 1998, 10 pgs.
Gandolfi, Sara, "The Proteasome and Proteasome Inhibitors in Multiple Myeloma", Cancer Metastasis Rev. 36 4, pp. 561-584, [Online] Retrieved from the internethttps doi.org 10.1007 s10555-017-9707-8, Dec. 2, 2017, 24 pgs.
Han, Yong Hwan, "MG132 as a Proteasome Inhibitor Induces Cell Growth Inhibition and Cell Death in A549 Lung Cancer Cells via Influencing Reactive Oxygen Species and GSH Level", Hum. Exp. Toxicol. 29 7, pp. 607-614, [Online] Retrieved from the internethttps doi.org 10.1177 0960327109358733, 2010, 8 pgs.
Huang, X, "An Atomic Structure of the Human 26S Proteasome", Nat. Struct. Mol. Biol. 23 9, [Online]. Retrieved from the Internet https doi.org 10.1038 nsmb.3273, 2016, 10 pgs.
Jones, Corey L., "Small Molecule Enhancement of 20S Proteasome Activity Targets Intrinsically Disordered Proteins", ACS Chem Biol., 129, [Online]. Retrieved from the Internet URL https doi.org 10.1021 acschembio.7b00489., 2017, 2240-2247.
Kisselev, A. F., "Monitoring Activity and Inhibition of 26S Proteasomes With Fluorogenic Peptide Substrates", Methods in Enzymology, vol. 398, 364-378, [Online]. Retrieved from the Internet URL https doi.org 10.1016 S0076-68790598030-0, 2005, 15 pgs.
Kuhn, Deborah J, "Potent activity of carfilzomib, a novel, irreversible inhibitor of the ubiquitin-proteasome pathway, against preclinical models of multiple myeloma", Blood 110 9, pp. 3281-3290, [Online] Retrieved from the internethttps doi.org 10.1182 blood-2007-01-065888, Jun. 25, 2007, 10 pgs.
Kumatori, A, "Abnormally High Expression of Proteasomes in Human Leukemic Cells", Proc. Natl. Acad. Sci. 87 18, [Online]. Retrieved from the Internet https doi.org 10.1073 pnas.87.18.7071, 5 pgs.
Leestemaker, Y, "Proteasome Activation by Small Molecules", Cell Chem. Biol. 24 6, [Online]. Retrieved from the Internet https doi.org 10.1016 j.chembiol.2017.05.010, 2017, 20 pgs.
Liu, Chang-Wei, "A Precipitating Role for Truncated a-Synuclein and the Proteasome in a-Synuclein Aggregation", Implications for Pathogenesis of Parkinson Disease, J. Biol. Chem, 22670-22678, [Online]. Retrieved from the Internet URL https doi.org 10.1074 jbc.M501508200, 2005, 9 pgs.
Meng, Lihao, "Epoxomicin, a potent and selective proteasome inhibitor, exhibits in vivo antiinflammatory activity", Proc Natl Acad Sci U S A, 9618, Aug. 31, 1999, 10403-10408.
Neilsen, Paul M, "New 26S Proteasome Inhibitors with High Selectivity for Chymotrypsin-Like Activity and p53-Dependent Cytotoxicity", ACS Chem. Biol. 2013, 8 2, pp. 353-359, [Online] Retrieved from the internethttps doi.org 10.1021 cb300549d, Nov. 28, 2012, 7 pgs.
Noda, Chiseko, "Tissue Distribution of Constitutive Proteasomes, Immunoproteasomes, and PA28 in Rats", Biochemical and Biophysical Research Communications 277, pp. 348-354, [Online] Retrieved from the internethttps doi.org 10.1006 bbrc.2000.3676, Sep. 20, 2000, 7 pgs.
Orlowski, R Z, "The Role of the Ubiquitination-Proteasome Pathway in Breast Cancer Applying Drugs That Affect the Ubiquitin-Proteasome Pathway to the Therapy of Breast Cancer", Breast Cancer Res. 5 1, [Online]. Retrieved from the Internet https doi.org 10.1186 bcr460, 2002, 7 pgs.
Richardson, Paul G, "Bortezomib PS-341 A Novel, First-in-Class Proteasome Inhibitor for the Treatment of Multiple Myeloma and Other Cancers", Cancer Control J. Moffitt Cancer Cent. 10 5, pp. 361-369, [Online] Retrieved from the internethttps doi.org 10.1177 107327480301000502, 2003, 9 pgs.
Rodgers, Kenneth J, "Assessment of proteasome activity in cell lysates and tissue homogenates using peptide substrates", Int. J. Biochem. Cell Biol. 35 5, pp. 716-727, [Online] Retrieved from the internethttps doi.org 10.1016 S1357-27250200391-6, 2003, 12 pgs.
Spataro, V, "The Ubiquitin-Proteasome Pathway in Cancer", Br. J. Cancer 77 3, [Online]. Retrieved from the Internet https doi.org 10.1038 bjc. 1998.71, 1998, 8 pgs.
Stein, R L, "Kinetic Characterization of the Chymotryptic Activity of the 20S Proteasome", Biochemistry, 35 13, [Online] Retrieved from the internethttps doi.org 10.1021 bi952262x, 1996, 10 pgs.
Trader, D J, "Establishment of a Suite of Assays That Support the Discovery of Proteasome Stimulators", Biochim. Biophys. Acta BBA—Gen. Subj. 1861 4, [Online]. Retrieved from the Internet https doi. org 10.1016 j.bbagen.2017.01.003, 2017, 8 pgs.
Urru, Silvana A M, "A New Fluorogenic Peptide Determines Proteasome Activity in Single Cells", J. Med. Chem. 53 20, pp. 7452-7460, [Online] Retrieved from the internethttps doi.org 10.1021 jm100362x, Mar. 22, 2010, 9 pgs.
Zerfas, Breanna L, "Synthesis and Application of an Activity-Based Peptide-Peptoid Hybrid Probe for the Immunoproteasome", Current Protocols in Chemical Biology e76, vol. 11 4, [Online] Retrieved from the internethttps doi.org 10.1002 cpch.76, 2019, 22 pgs.

* cited by examiner

ACTIVITY-BASED PROBES WITH UNNATURAL AMINO ACIDS TO MONITOR PROTEASOME ACTIVITY

CROSS REFERENCE TO RELATED APPLICATIONS

This application is U.S. National Stage Filing under 35 U.S.C. 371 of International Patent Application Serial No. PCT/US2021/021950, filed Mar. 11, 2021, and published as WO 2021/183789 A1 on Sep. 16, 2021, which claims priority to U.S. provisional patent application No. 62/987,919, which was filed on Mar. 11, 2020, both of which are hereby incorporated by reference in their entirety.

STATEMENT OF GOVERNMENT SUPPORT

This invention was made with government support under GM131206 awarded by the National Institutes of Health. The government has certain rights in the invention.

INCORPORATION BY REFERENCE OF SEQUENCE LISTING

A Sequence Listing is provided herewith as a text file, “2123125.txt” created on Mar. 9, 2021 and having a size of 4,096 bytes. The contents of the text file are incorporated by reference herein in their entirety.

BACKGROUND

Eukaryotic cells rely on the proteasome, a large enzyme complex with various catalytic, activities, to maintain healthy protein levels and control a wide range of cell cycle pathways. Specifically, the 26S proteasome, comprised of the 19S regulatory particle (19S RP) and the 20S core particle (20S CP), degrades proteins that are damaged or otherwise no longer required. Such proteins are tagged for degradation with a chain of ubiquitin (Ub) monomers, which is recognized and removed by the 19S RP before the protein is shuttled into the 20S CP to be hydrolyzed into small peptide units. The resulting peptide products can then be recycled for the synthesis of new proteins or other purposes as the cell needs.

The improper regulation of the hydrolysis activity of the proteasome has been implicated in several different disease types. This includes numerous cancers, which require a higher level of protein degradation to keep up with their increased protein load, and protein aggregation disorders, which have been observed to have decreased proteasome activity for various reasons. As such, the proteasome has been recognized as a critical therapeutic target. For the past several decades, proteasome inhibitors have been studied and verified as a useful approach for the treatment of a variety of hematological cancers with the approval of bortezomib by the FDA for the treatment of multiple myeloma in 2003. In more recent years, small molecules which can stimulate the activity of the proteasome have also been discovered, providing a potential approach for the treatment of protein aggregation disorders, such as Parkinson's disease.

Shortly after the discovery of the proteasome, a fluorescent substrate probe was described which can be used to monitor the protease-like activity of the 20S CP. This probe contains a modified four-mer peptide, with the sequence succinyl-Leu-Leu-Val-Tyr (Suc-LLVY; SEQ ID NO: 1), conjugated to a 4-amino-7-methylcoumarin (AMC) molecule (FIG. 1A). In this structure, the amidation of the AMC molecule quenches its fluorescence, which can be restored upon the recognition of the peptide and cleaving of the Tyr-AMC amide bond. Since the initial reporting of the Suc-LLVY-based probe, other peptide-AMC structures have been designed, and made commercially available, which are selective for the specific protease-like subunits of the 20S CP. Together, these AMC-based substrate probes have been vital tools for understanding a range of characteristics of the proteasome, and have been especially important in studying proteasome inhibitors.

Although proven to be essential tools, these AMC-based probes suffer from several limitations. For example, the poor fluorescence properties of AMC require the use of high concentrations of the given probe in order to obtain suitable signals for in cell assays. At these concentrations, it is highly likely they are being cleaved by other cellular proteases and proteases in the cell media. To circumvent this issue, assays can be performed using cell lysate and generic proteases inhibitors, but it makes the evaluation of the effect of small molecule modulators of the proteasome confusing to assess. Although activity-based probes selective for different proteasome β-subunits have been described, they still are typically used with cell lysate and need to be repeated to include proteasome inhibitors to determine how much is attributed to non-proteasomal cleavage or lower molecular weight proteases must be removed from the lysate before assay preparation. To overcome some these concerns, Urru and co-workers developed a Förster resonance energy transfer (FRET)-based probe with improved selectivity. However, to obtain suitable cell permeability, a peptide sequence corresponding to residues 48-57 of TAT was included at the C-terminus, creating a probe which is 20 residues long and is cumbersome to synthesize making its application for a high throughput screen challenging.

A more effective activity-based probe to monitor proteasome activity, with the goal of using it for various applications, including the evaluation of inhibitors and stimulators, in live cells remains a need. This would require a structure which is more selective for the proteasome over other cellular proteases to decrease background fluorescence and has sufficient cell permeability to perform assays at lower concentrations as compared to the AMC-containing probes. Further the probe could be sensitive to both inhibitors and stimulators, providing a tool that could evaluate and Quantitate the real-time cleavage activity of the proteasome in a variety of cell types.

SUMMARY

The disclosure relates to a compound of formula (I):

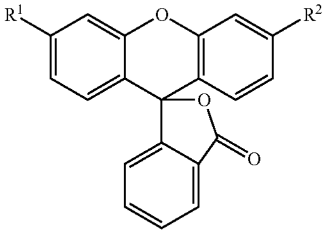

wherein:

$R^1$ is $A_1$-$A_2$-$A_3$-$A_4$* (SEQ ID NO: 2) or $A_1$-$A_2$-$A_3$-$A_4$-$A^5$* (SEQ ID NO: 2);

$R^2$ is:

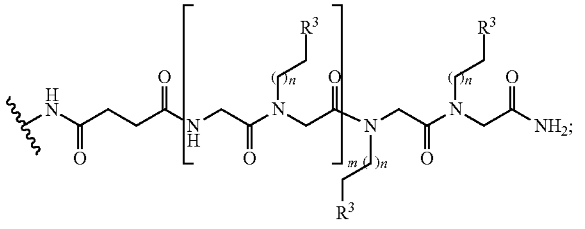

each $R^3$ is independently —$N(CH_3)_2$ or —$OCH_3$;

$A_1$ is Len or Ac;

$A_2$ is Leu, Gly, Arg;

$A_3$ is Val, Pro, or Leu;

$A_4$ is Tyr, Leu, or Arg;

$A_5$ is Asp;

each instance of n is independently 1, 2, 3; and m is 1, 2, 3.

The disclosure further relates to uses of compounds of formula (I) for Compounds of Formula (I) can also be used directly in cells to monitor the real time increase in proteasome activity.

Compounds of Formula (I) can be used to distinguish the different levels of proteasome, activities between cancer cell lines in real time.

Compounds of Formula (I) can be used to monitoring the effects of small molecule stimulators of the proteasome in live cells and comparing the relative proteasome activity across different cancer cell types Compounds of Formula (I) can also be used to evaluate both small molecule inhibitors and stimulators of the proteasome, allowing the discovery of two classes of small molecule modulators of proteasome activity from a single screening campaign.

Compounds of Formula (I) can also be used as tools to support the discovery and characterization of small molecule modulators of proteasome activity Compounds of Formula (I) can also be used directly in cells to monitor the real time increase in proteasome activity Compounds of Formula (I) can be used in a variety of cell lines and in combination with other activity-based probes or cell markers.

Compounds of Formula (I) can be used to determine the threshold of proteasome activity required for a cancer cell type to be highly susceptible to proteasome inhibitors.

Compounds of Formula (I) can be used to validate new proteasome inhibitors if their toxicity correlates with a decrease in proteasome activity or if there are potential off-target effects.

Compounds of Formula (I) can be effective for cell-based proteasome inhibitor screens. Performing a screening assay in cells rather than with purified proteasome can allow the evaluation of the cell-permeability of the inhibitor, eliminating the need to follow-up with primary hits that then are only demonstrated to work in the biochemical assay.

Compounds of Formula (I) can be used for the detection of weak inhibitors. Weak inhibitors can have scaffolds that have not been considered as potential proteasome inhibitors.

All three probes were able to detect stimulation is determined by an increase in the % activity over 60 min as compared to the DMSO control. Both TAS1 and TAS3 can differentiate between weak (TRC-1 and TCM-1) and strong proteasome stimulators (MK-886).

Figure 8:
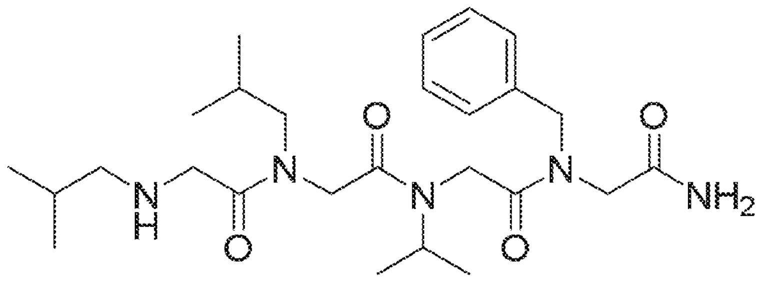
Figure 8:

FIG. 8 shows a peptoid containing amines withcorresponding functional groups to mimic a LLVF peptide sequence.

It is to be understood that the drawings are not intended to limit the scope of the present teachings in any way.

DETAILED DESCRIPTION

Compounds

The disclosure relates to a compound of formula (I):

(I)

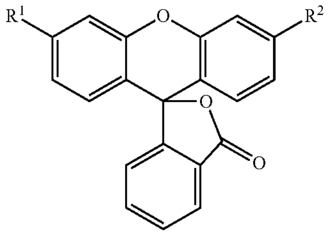

wherein:

$R^1$ is $A_1$-$A_2$-$A_3$-$A_4$* (SEQ ID NO: 2) or $A_1$-$A_2$-$A_3$-$A_4$-$A_5$* (SEQ ID NO: 2);

$R^2$ is:

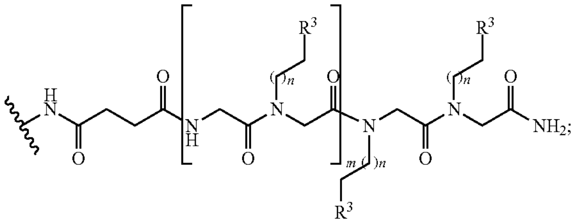

each $R^3$ is independently —$N(CH_3)_2$ or —$OCH_3$;

$A_1$ is Leu or Ac;

$A_2$ is Leu, Gly, or Arg;

$A_3$ is Val, Pro, or Len;

$A_4$ is Tyr, Len, or Arg;

$A_5$ is Asp;

each instance of n is independently 1, 2, 3; and m is 1, 2, 3$A_1$ can be Leu. $A_1$ can be Ac.

$A_2$ can be Leu. $A_2$ can be Gly. $A_2$ can be Arg.

$A_3$ can be Val. $A_3$ can be Pro, $A_3$ can be Leu.

$A_4$ can be Tyr. $A_4$ can be Leu. $A_4$ can be Arg.

$R^3$ can be —$N(CH_3)_2$. $R^3$ can be —$OCH_3$. At least one instance of $R^3$ can be —$N(CH_3)_2$. All instances of $R^3$ can be —$N(CH_3)_2$. At least one instance of $R^3$ can be —$OCH_3$. All instances of $R^3$ can be —$OCH_3$.

m can be 1.m can be 2.m can be 3.

n can be 1.n can be 2.n can be 3. All instances of n can be the same. All instances of n can be different. At least two instances of n can be the same. At least two instances of a can be different.

$R^2$ can be

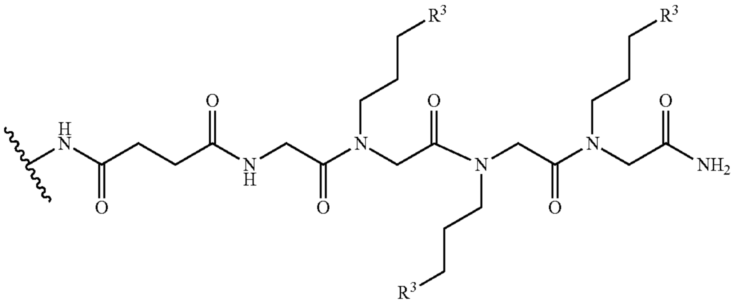

or

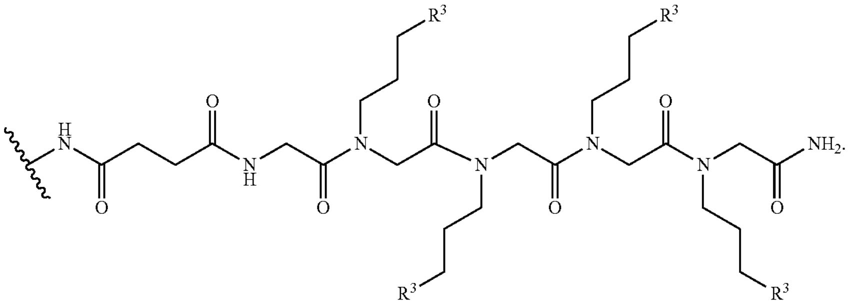

A compound of Formula, (I) can be selected from:

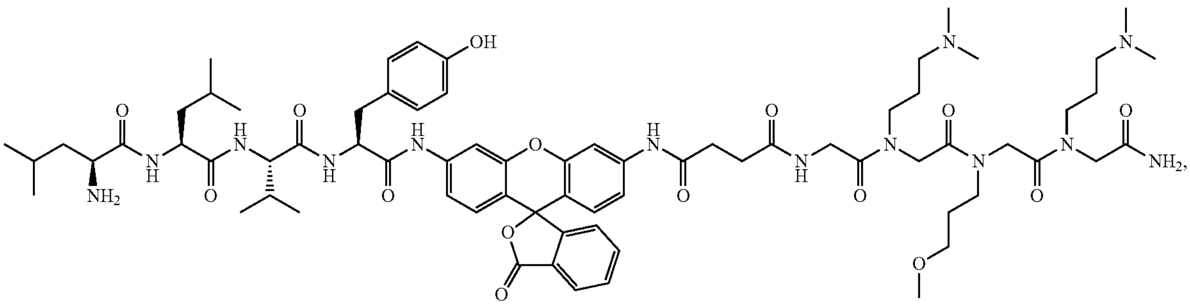

,

-continued
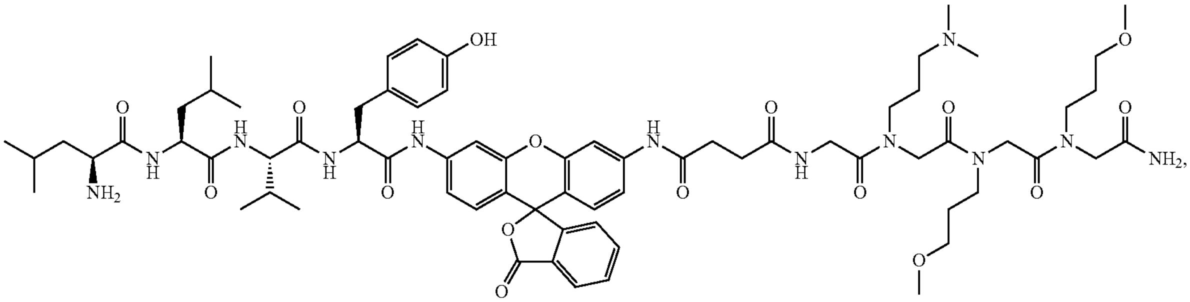
,
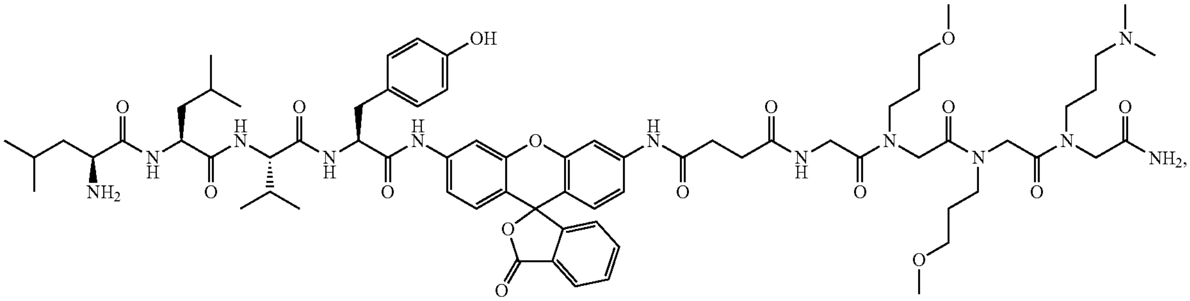
,
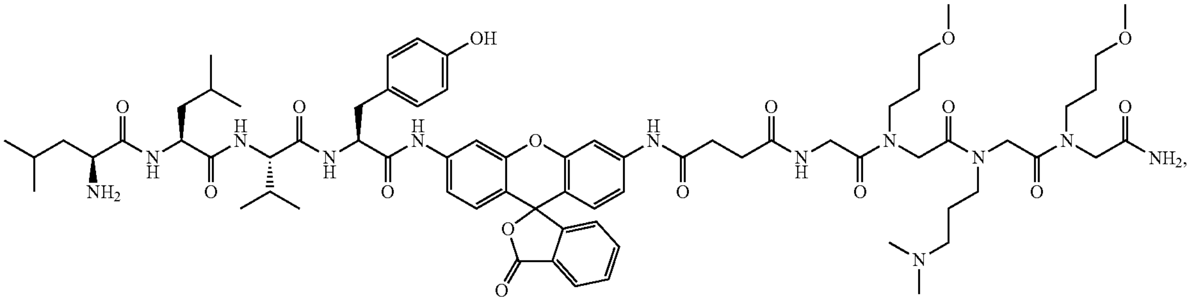
,
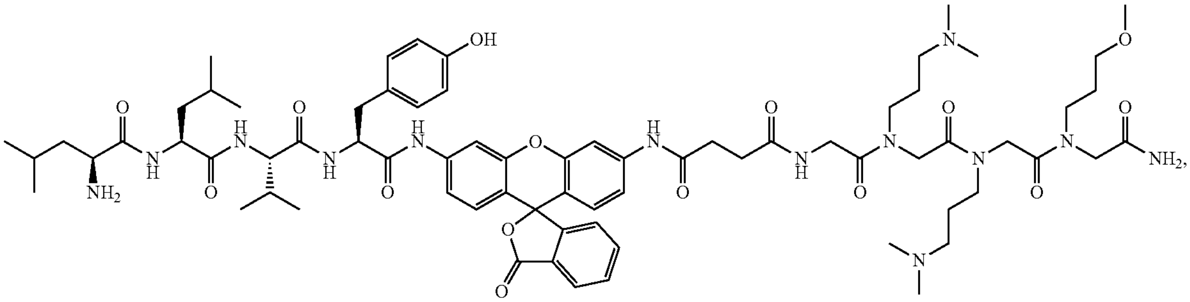
,
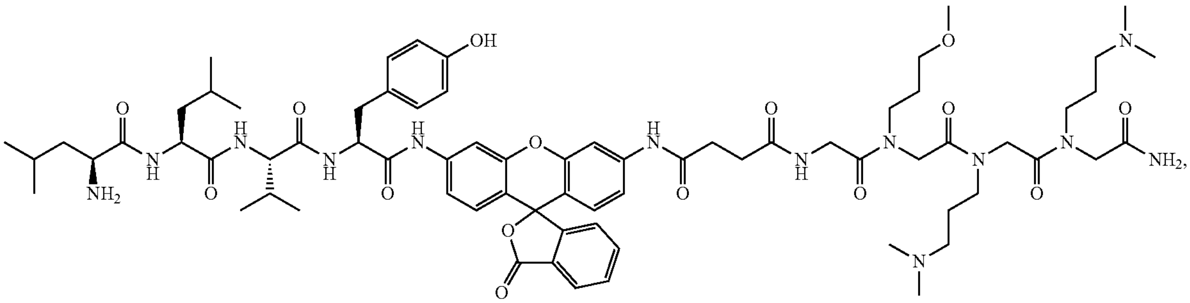
,

-continued
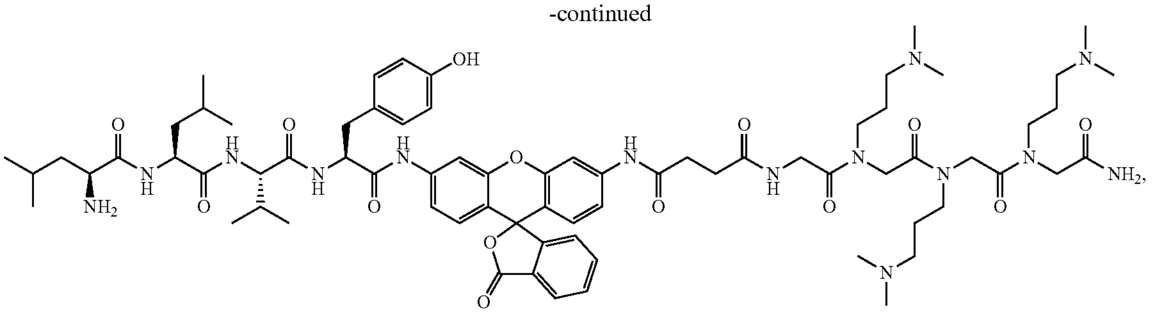
and
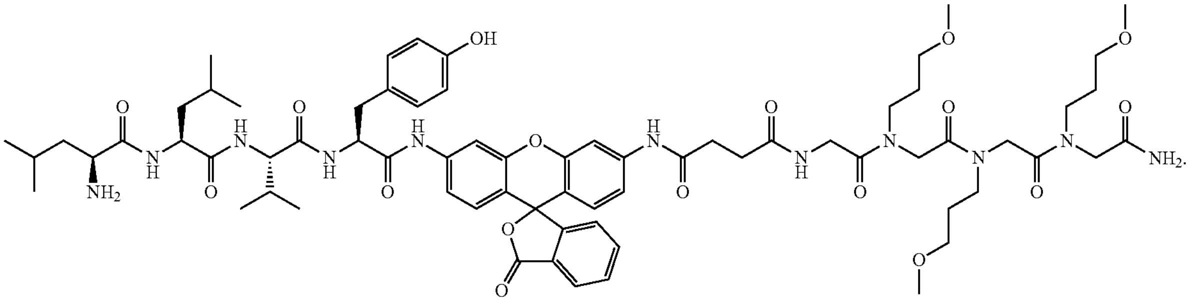
A compound of Formula (I) can be selected from:
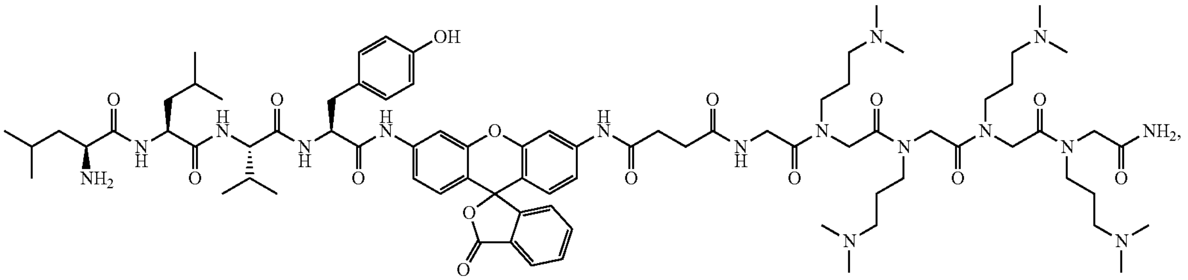
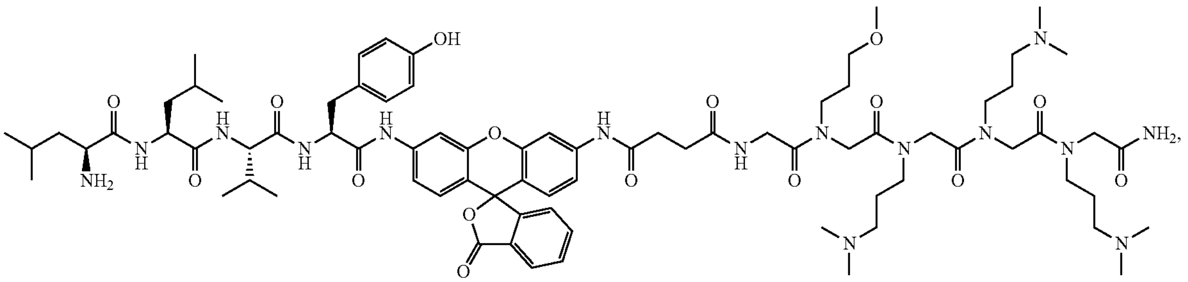
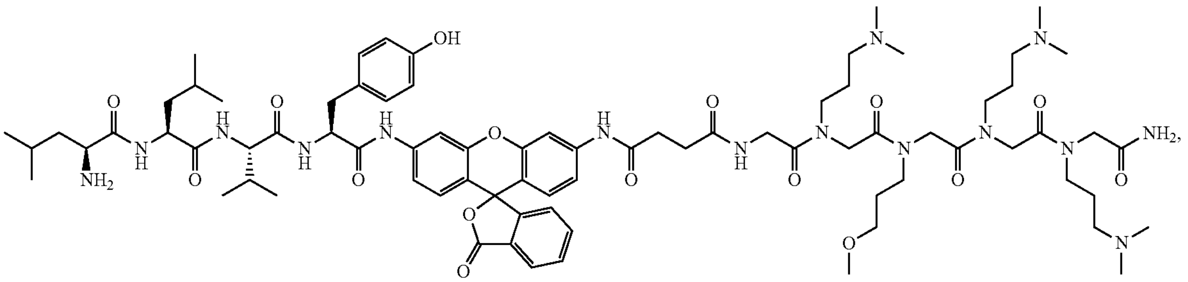

-continued
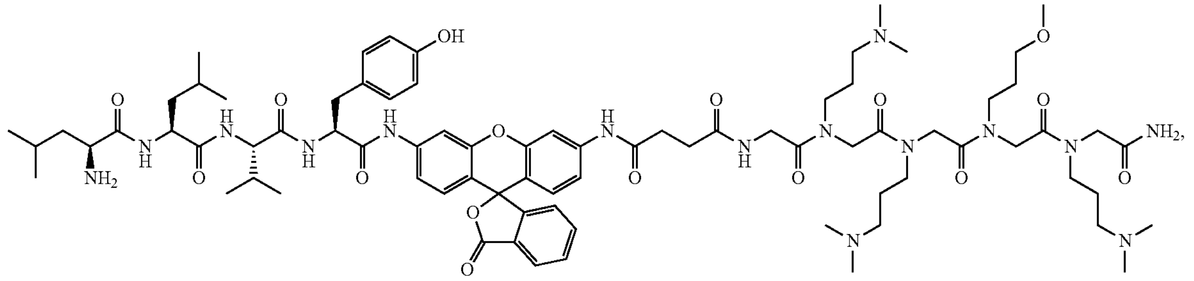
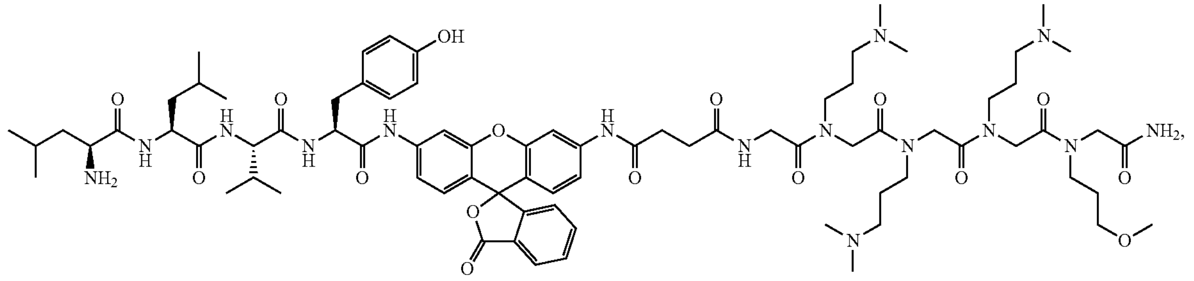
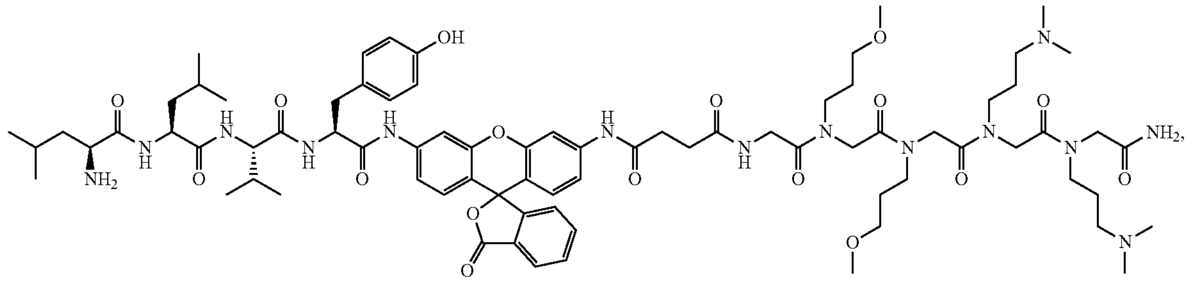
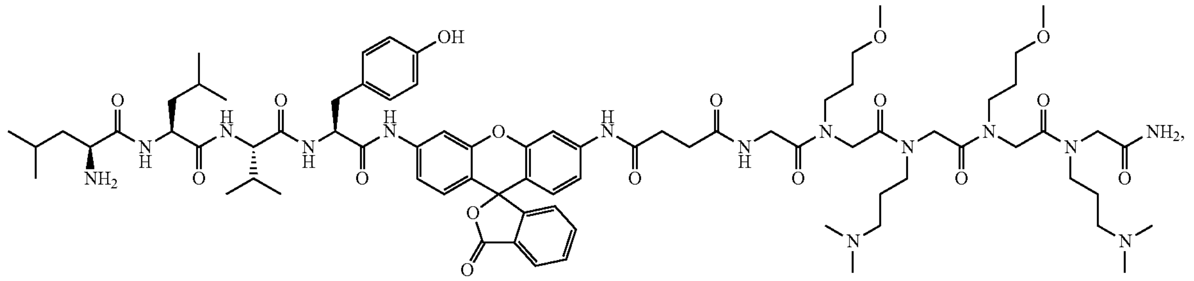
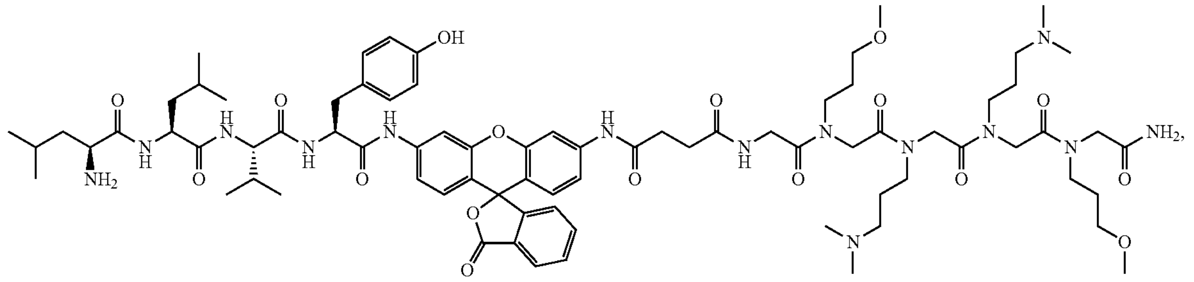 [SMILES: COCCCN(CC(N)=O)C(=O)CN(CCCOC)C(=O)CN(CCCOC)C(=O)CN(CCCOC)C(=O)CNC(=O)CCC(=O)Nc1ccc2c(c1)Oc1cc(NC(=O)[C@H](Cc3ccc(O)cc3)NC(=O)[C@@H](NC(=O)[C@H](CC(C)C)NC(=O)[C@@H](N)CC(C)C)C(C)C)ccc1C21OC(=O)c2ccccc21]
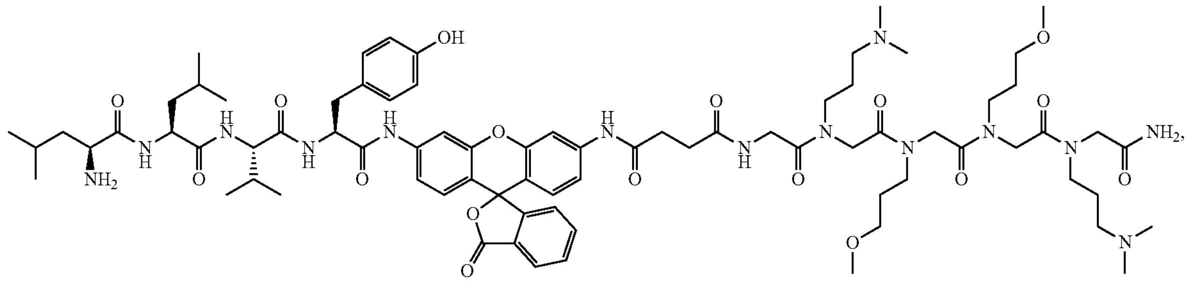

-continued
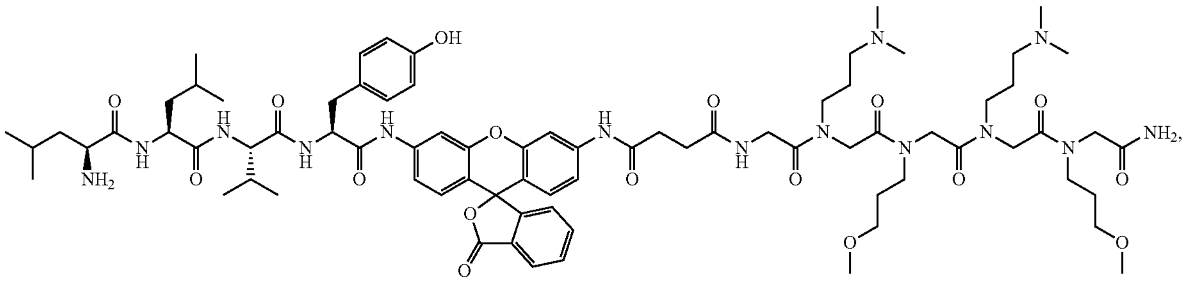
,
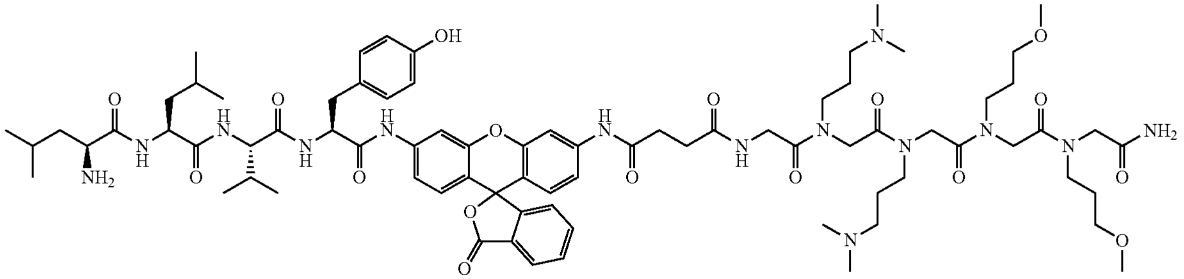
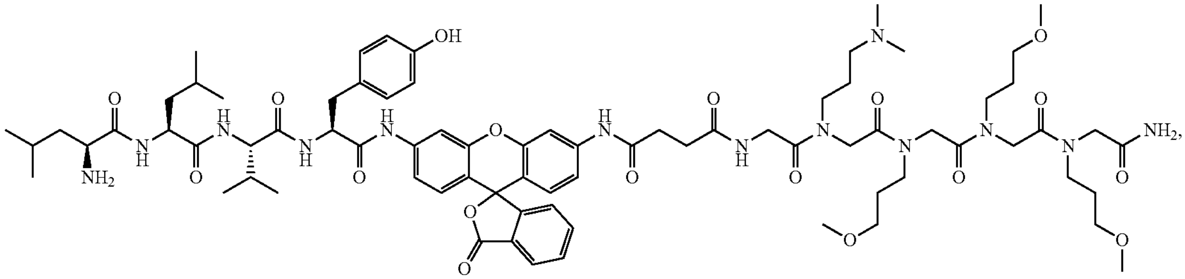
,
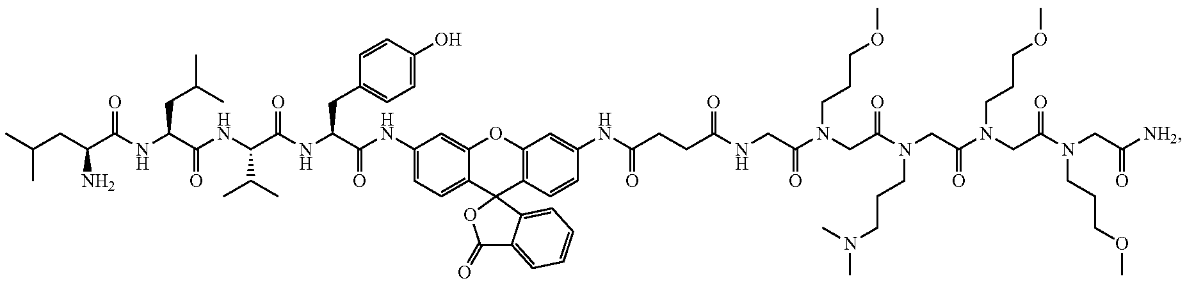
,
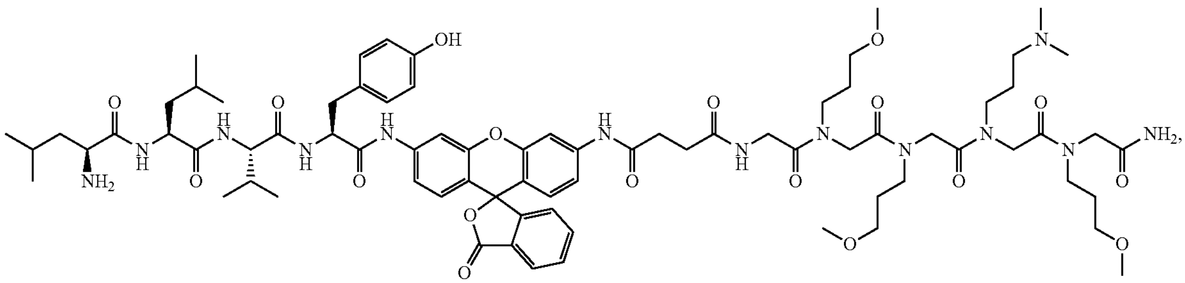
,
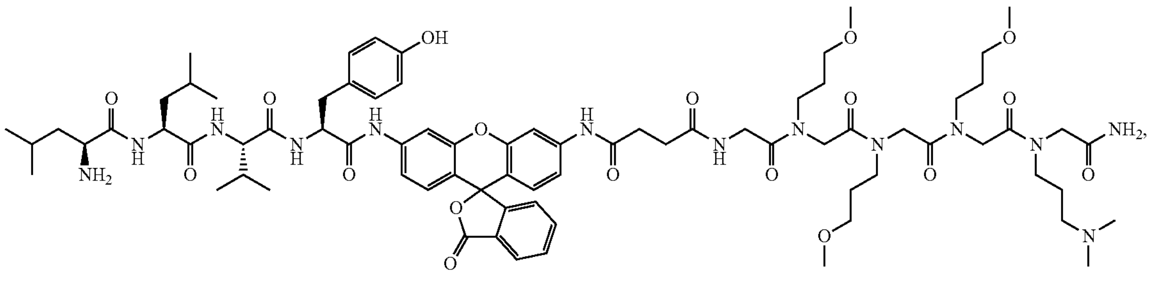
, and -continued

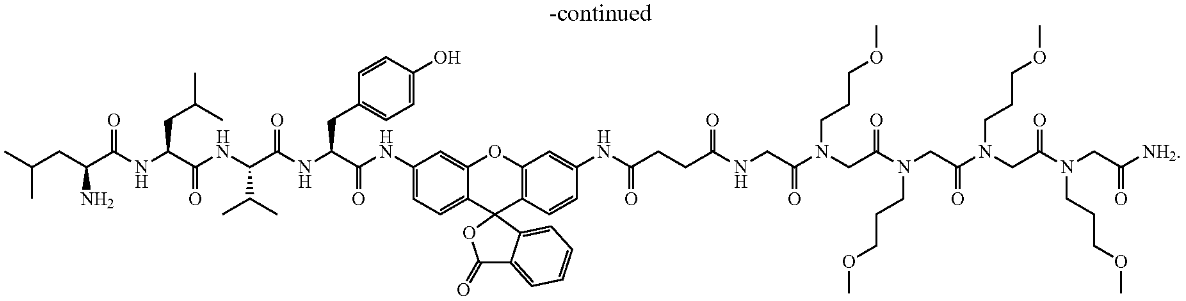

A compound of Formula (I) can be

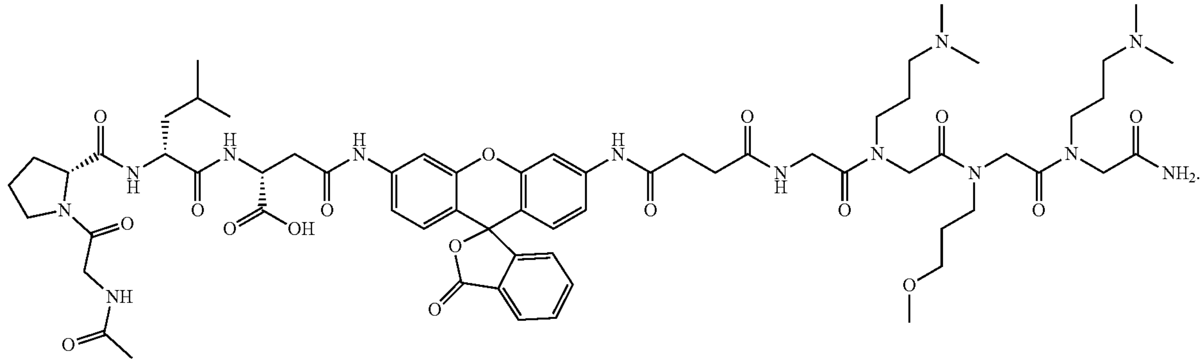 [SMILES: COCCCN(CC(=O)N(CCCN(C)C)CC(N)=O)C(=O)CN(CCCN(C)C)C(=O)CNC(=O)CCC(=O)Nc1ccc2c(c1)Oc1cc(NC(=O)C[C@@H](NC(=O)[C@@H](CC(C)C)NC(=O)[C@H]3CCCN3C(=O)CNC(C)=O)C(=O)O)ccc1C21OC(=O)c2ccccc21]

A compound of Formula, (I) can be

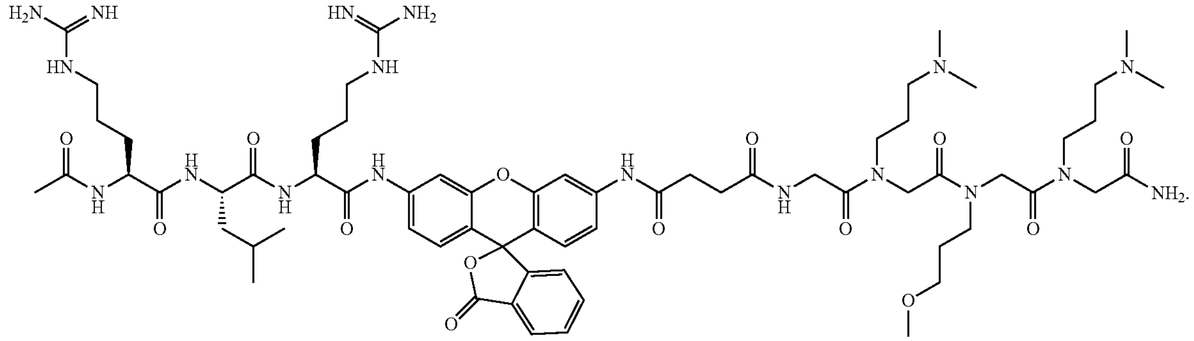 [SMILES: COCCCN(CC(=O)N(CCCN(C)C)CC(N)=O)C(=O)CN(CCCN(C)C)C(=O)CNC(=O)CCC(=O)Nc1ccc2c(c1)Oc1cc(NC(=O)[C@H](CCCNC(=N)N)NC(=O)[C@H](CC(C)C)NC(=O)[C@H](CCCNC(=N)N)NC(C)=O)ccc1C21OC(=O)c2ccccc21]

Compounds of Formula (I) can show resistance to cleavage leading to a fluorescent signal by proteases in human serum, demonstrating improved selectivity.

Compound of Formula (I) can have improved fluorescence properties and selectivity towards the proteasome compared to other cellular proteases Compounds of Formula (I) can be highly sensitive in the detection and/or quantification of proteasome activity. The sensitivity can be 50-2000 RFU/min, such as 100-200 RFU/min, 100-500 RFU/min, 100-1000 RFU/min, and 500-1000 RFU/min.

The quantification can be 500-7000 RFU/min, such as 1000-6000 RFU/min, 1000-5000 RFU/min, 1000-2000 RFU/min, and 2000-6000 RFU/min.

Uses and Methods

Compounds of Formula (I) can also be used directly in cells to monitor the real time increase in proteasome activity.

Compounds of Formula (I) can be used to distinguish the different levels of proteasome activities between cancer cell lines in real time.

Compounds of Formula (I) can be used to monitoring the effects of small molecule stimulators of the proteasome in live cells and comparing the relative proteasome activity across different cancer cell types Compounds of Formula (I) can also be used to evaluate both small molecule inhibitors and stimulators of the proteasome, allowing the discovery of two classes of small molecule modulators of proteasome activity from a single screening campaign.

Compounds of Formula (I) can also be used as tools to support the discovery and characterization of small molecule modulators of proteasome activity Compounds of Formula (I) can also be used directly in cells to monitor the real time increase in proteasome activity Compounds of Formula (I) can be used in a variety of cell lines and combination with other activity-based probes or cell markers.

Compounds of Formula (I) can be used to determine the threshold of proteasome activity required for a cancer cell type to be highly susceptible to proteasome inhibitors.

Compounds of Formula (I) can be used to validate new proteasome inhibitors if their toxicity correlates with a decrease in proteasome activity or if there are potential off-target effects.

Compounds of Formula (I) can be effective for cell-based proteasome inhibitor screens. Performing a screening assay in cells rather than with purified proteasome can allow the evaluation of the cell-permeability of the inhibitor, eliminating the need to follow-up with primary hits that then are only demonstrated to work in the biochemical assay.

Compounds of Formula (I) can be used for the detection of weak inhibitors. Weak inhibitors can have scaffolds that have not been considered as potential proteasome inhibitors.

Compound of Formula (I) can be use to monitor proteasome activity in diverse settings like, such as but not limited to biochemical assays, animal samples (cells/tissues), human samples (cells/tissues), in healthy and disease states, and the like.

The disclosure relates to a method of monitoring the real time increase in proteasome activity in cells comprising contacting the cells with a compound of formula (I) and measuring proteasome activity by the accumulation of a fluorescent signal.

The disclosure also relates to a method of differentiating levels of proteasome activities between cancer cell lines in real time.

The disclosure relates to a method of monitoring the effects of small molecule stimulators of the proteasome in live cells and comparing the relative proteasome activity across different cancer cell types.

The disclosure relates to a method of evaluate both small molecule inhibitors and stimulators of the proteasome from a single screening campaign.

The disclosure relates to a method of determining the threshold of proteasome activity required for a cancer cell type to be highly susceptible to proteasome inhibitors.

Definitions

Unless defined otherwise, all technical and scientific terms used herein have the same meaning as commonly understood by one of skill in the chemical and biological arts. Additionally, as used in this specification and the appended claims, the singular forms "a", "an" and "the" include plural referents unless the content clearly dictates otherwise. Thus, for example, where a compound/composition is substituted with "an" alkyl or aryl, the compound/composition is optionally substituted with at least one alkyl and/or at least one aryl. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

The term "probe" or "compound" relate to compound of Formula (I).

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

"Quantification" is the change in relative fluorescent units (RFU) per time unit.

"Sensitivity" is at least a 5% increase in activity as compared to the DMSO control.

It will be understood by one of ordinary skill in the relevant arts that other suitable modifications and adaptations to the compositions and methods described herein are readily apparent from the description of the disclosure contained herein in view of information known to the ordinarily skilled artisan, and may be made without departing from the scope of the disclosure. Having now described the present disclosure in detail, the same will be more clearly understood by reference to the following examples, which are included herewith for purposes of illustration only and are not intended to be limiting of the disclosure.

EXAMPLES

The present disclosure can be better understood by reference to the following examples which are offered by way of illustration.

Figure 1:
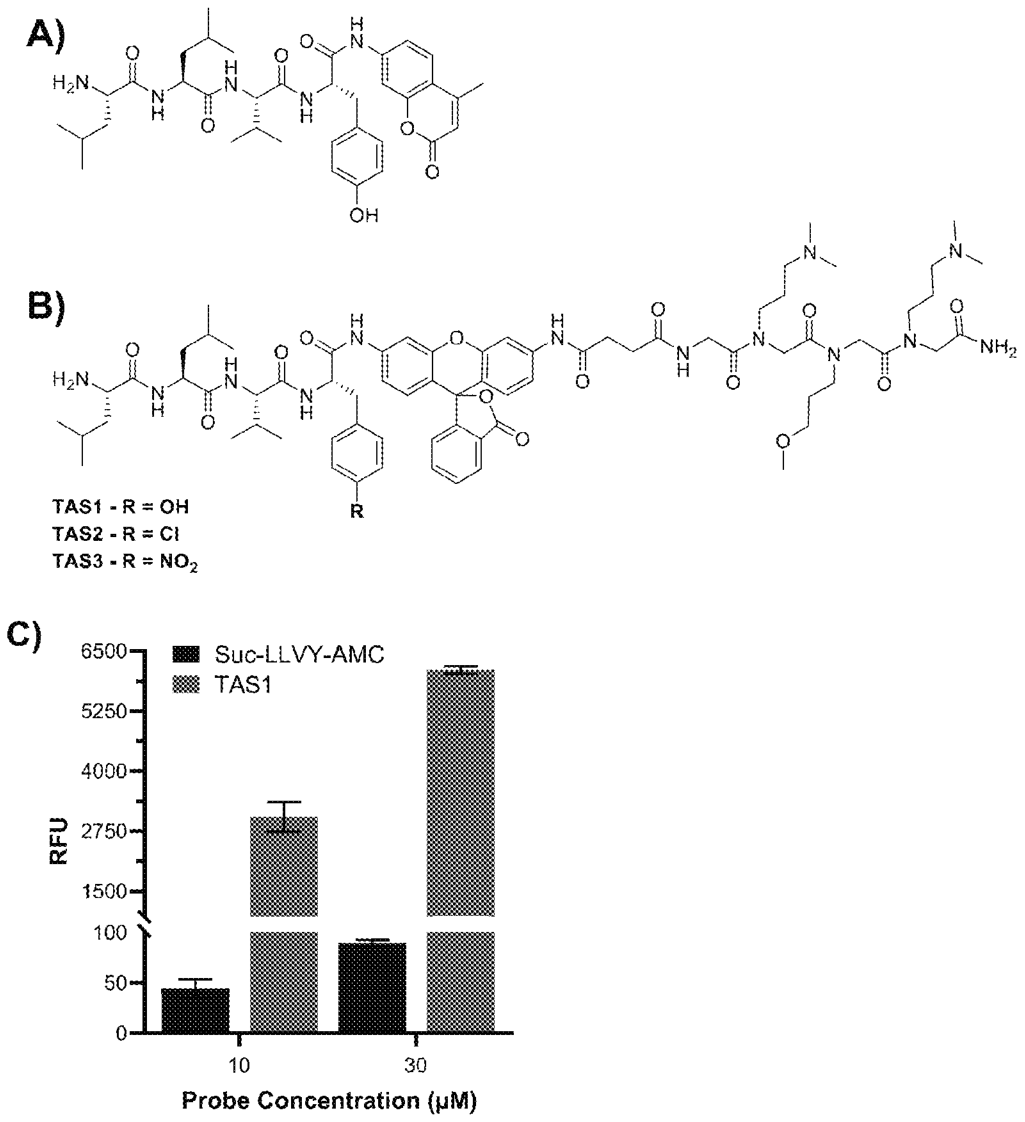
FIG. 1A is the structure of commercially available Suc-LLVY-AMC (SEQ ID NO: 1).
FIG. 1B is the structure of Rh-based peptide/peptoid hybrid probe.
FIG. 1C is a graph of the fluorescence signal when comparing Suc-LLVY-AMC (SEQ ID NO: 1) to TAS1 with purified 20S CP.
Figure 2:
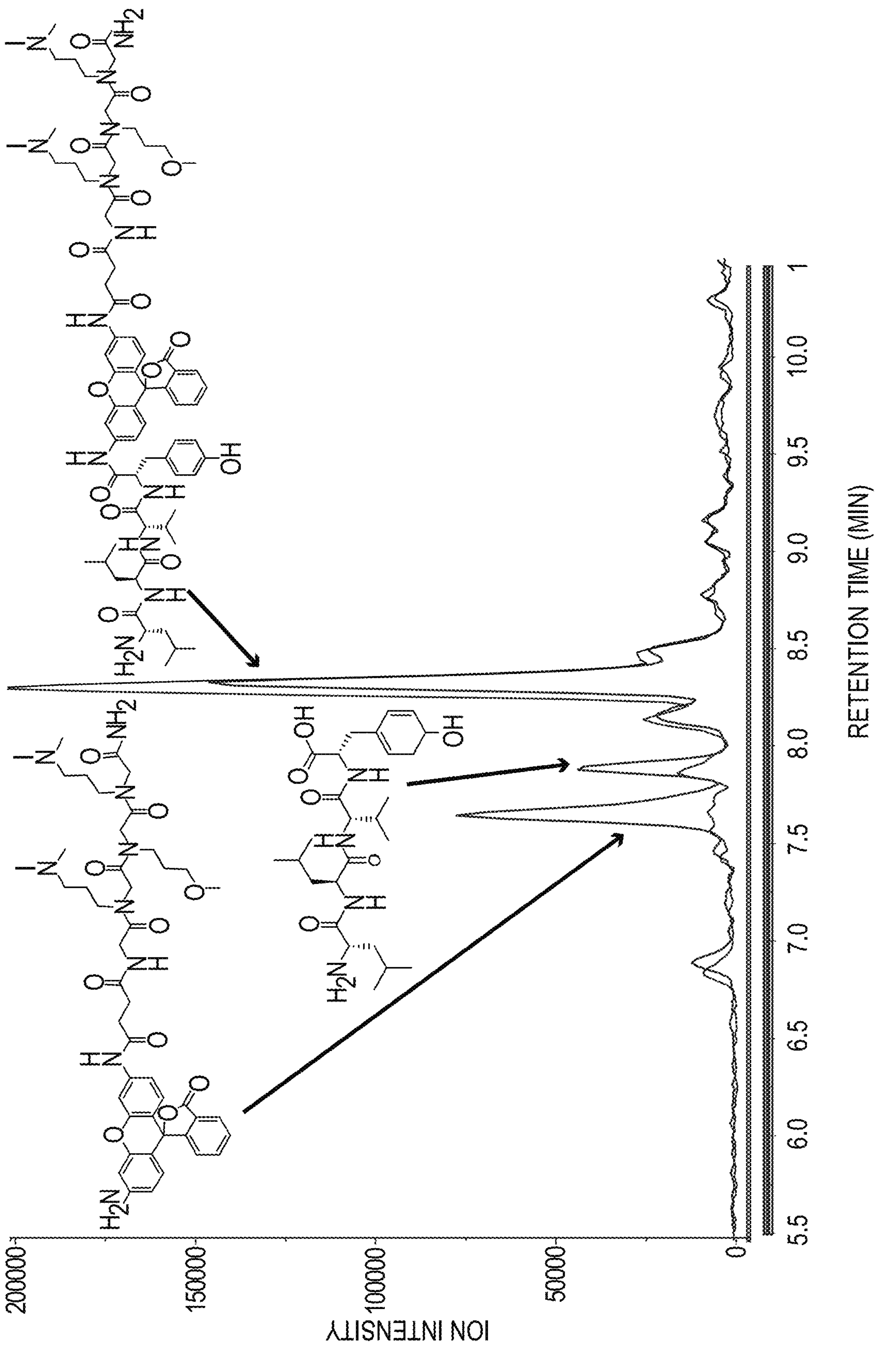
FIG. 2 is a chromatogram of the ion intensity over the retention time of representation compounds. After incubating for 2 hours with 20S CP, samples of 30 μM TAS1 were analyzed by LC/MS to determine if the expected cleavage products were produced. Shown are example TIC traces for untreated (black) and 20S CP-treated (red). In the treated samples, we only observed two new peaks, corresponding to the 4-mer peptide and fluorescent Rh-peptoid fragments, along with a decrease in the full length TAS1. Corresponding structures are shown for each peak.

Example 1—Activity-Based Probes with Unnatural Amino Acids to Monitor the Proteasome in Live Cells The peptide recognition sequence used was based on the commercially available 4-mer AMC probe (FIG. 1A), specifically Leu-Leu-Val-Tyr (SEQ ID NO: 1), to generate TAS1 (FIG. 1B). To determine if TAS1 had any enhanced sensitivity, the two probes were compared under the same conditions with purified 20S CP. Briefly, the probes were incubated in triplicate at 10 and 30 μM with 9 nM 205 CP at 37° C. The change in fluorescence was monitored for two hours and the endpoint values were averaged and graphed for comparison (FIG. 1C). Because the two fluorophores have different excitation and emission wavelengths, the two experiments were performed separately but using the same conditions for the plate reader (i.e. gain, number of flashes, settling time, etc.). This data shows that TAS1 has a signal greater than Suc-LLVY-AMC (SEQ ID NO: 1) by more than an order of magnitude when used at either concentration. Since, unlike Suc-LLVY-AMC (SEQ ID NO: 1), TAS1 has the potential to have more than one cleavage site which could result in an increase in fluorescence (on either side of Rh110), we confirmed that the increase in signal is only from the recognition and cleavage of the peptide at the Tyr moiety by analyzing the 30 μM TAS1 samples by LC/MS (FIG. 2). This data showed that the only new peaks formed after incubating with purified 20S CP were the expected cleavage products, indicating that the fluorescence signal is not a result from cleavage of the bond between the Rh110 and the peptoid segment of TAS1.

One of the limitations to using activity-based probes for the proteasome in cells is the ability of proteases to also recognize and cleave at the desired amino acid, leading to a fluorescent signal. This non-proteasomal cleavage yields a falsely high fluorescence signal, requiring additional experiments to be able to properly interpret the data. For this reason, we were interested in determining if there were any unnatural amino acids that could be recognized by the proteasome and had preferred cleavage by the proteasome compared to other proteases in cells. For this, we chose to synthesize and evaluate a small library of peptides for their ability to act as 20S CP substrates using LC/MS, FIG. 3. We initially chose to vary the amino acid in the S1 position, replacing Tyr, as the recognition of this amino acid determines which β-subunit preferentially will cleave the peptide. The remainder of the 20S CP binding sequence was kept the same as TAS1. We also decided to exchange the Rh110-peptoid fragment with an Ala-Ala dipeptide, as a fluorescent signal was not required for our LC-MS-based quantitation assay. Since the peptide in TAS1 is recognized by the β5 active site, which has chymotrypsin-like activity, we focused our library on amino acids with larger, hydrophobic side chains, including various phenylalanine derivatives. In addition to non-canonical side chains, we were interested in whether the proteasome could recognize unnatural backbone structures, such as N-methylation and d-isomers. Overall, the library included 15 unique sequences, along with Tyr and Ala derivatives as positive and negative controls, respectively.

The peptides were synthesized in parallel fashion using standard Fmoc-based solid phase synthesis. Briefly, the Ala-Ala dipeptide was synthesized on a bulk amount of Rink Amide polystyrene resin. After Fmoc-removal, the resin was aliquoted equally for each library member. The corresponding Fmoc-protected amino acid (4 eq) was added to each resin aliquot along with HBTU (3.75 eq) and DIPEA (8 eq) in DMF. After the couplings were complete, the resin was kept separated and synthesis was continued for the remaining sequence. Each library member was cleaved using a TFA-cocktail and there purified using reverse-phase HPLC, confirming purity >95% by LC/MS.

To evaluate this set of peptides as potential 20S CP substrates, we applied a similar LC/MS-based assay to that used to discover the immunoproteasome probe. Briefly, the peptides were dissolved in DMSO at a stock concentration of 600 μM. The peptides were then diluted in 50 mM tris buffer, pH 7.4, in a 96-well plate for a final assay concentration of 12 μM in two sets of triplicates. One set of triplicates served as a negative control, incubated in tris buffer alone. For analysis, this would correspond to the ionization intensity of completely intact samples, which can then be compared to the amount of intact peptide remaining in 20S CP-treated samples. To the other triplicate was added 20S CP to a final concentration of 9 nM. All samples were incubated at 37° C. for one hour before an equal volume of acetonitrile was added to halt degradation by denaturing the 20S CP. Samples were dried, resuspended in 50/50 water/acetonitrile with 0.1% formic acid and analyzed by LC/MS (example spectra can be found in Supporting Information Appendix B).

Figure 4:
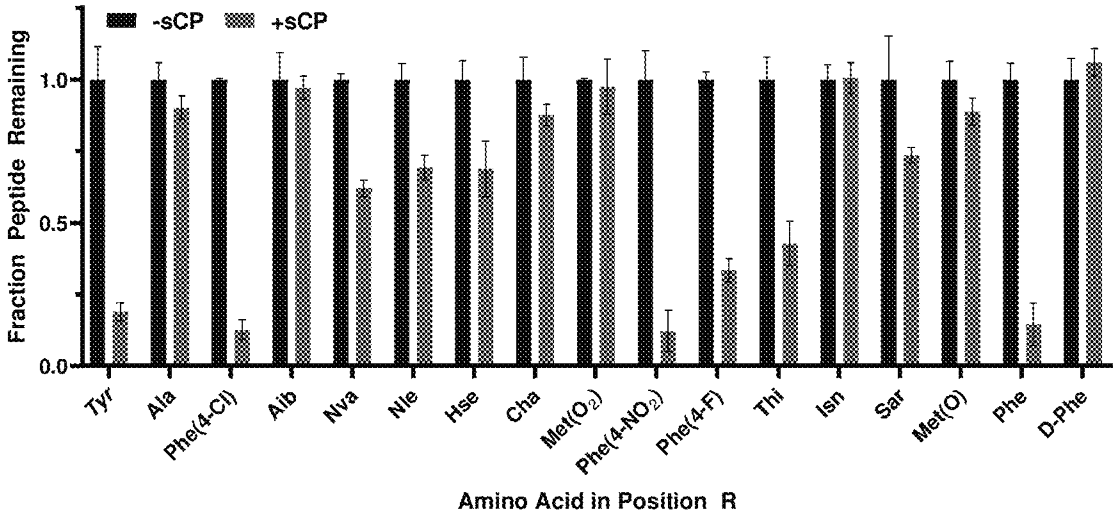
FIG. 4 is a bar graph of the fraction peptide remaining based on amino acid permutation. The mass of each uncleaved peptide was extracted from all corresponding samples. The average amount of peptide in untreated samples were scaled to 1 and the treated samples were scaled accordingly from this. All samples are shown as an average of triplicates.

For each peptide, the mass of the full (uncleaved) structure was extracted (extracted ion chromatogram, EIC) from each sample and this peak was integrated to obtain the peak area. The peak areas for the negative control samples of individual structures were averaged and set to 1. Peak areas for 20S CP-treated samples were then scaled to the average for the untreated sample and the triplicates averaged to obtain a value for the fraction of full peptide remaining (FIG. 4). To confirm that the peptide was being cleaved at the desired position, the mass of the corresponding 4mer-peptide cleavage product was found in each 20S CP-treated sample with significant decrease in full peptide observed.

Of the structures tested, ten had a significant decrease in the amount of full peptide remaining compared to their respective untreated samples, while three peptides were better cleaved than the Tyr positive control. The library members containing unnatural backbone linkages showed mixed results, the sarcosine (Sar) peptide was determined to be significantly cleaved, while the 20S CP did not accept the peptide with the D-Phe moiety. After obtaining this promising result for Sar, we synthesized a peptoid containing amines with corresponding functional groups to mimic a LLVF peptide sequence (FIG. 8) to determine if this result was exclusive to Sar and with the hypothesis that spatially shifting these groups equally would still allow for them to interact with the proteasome substrate binding pockets. Unfortunately, no significant cleavage was observed for this structure.

We observed that the aromatic structures, including all Phe analogues as well as thienylalanine (Thi), had the highest amount of cleavage. By comparing Phe to cyclohexylalanine (Cha), the favorable cleavage of these aromatic derivatives could be contributed to by their planar configurations. A comparison can also be made between the non-branched alkyl side chains: norvaline (Nva), norleucine (Me) and homoserine (Hse) all have close to 50% cleavage, while Ala is observed to have less than 10% of the peptide cleaved. This suggests that, while not cleaved as well as the aromatic functional groups, alkyl groups of a certain length can also be recognized by the 20S CP and hydrolyzed, Considering these results, we selected the five peptides cleaved more than 50%, as well as Sar since it was the only structure with an unnatural backbone to have significant cleavage observed, to test for human serum stability.

Figure 5:
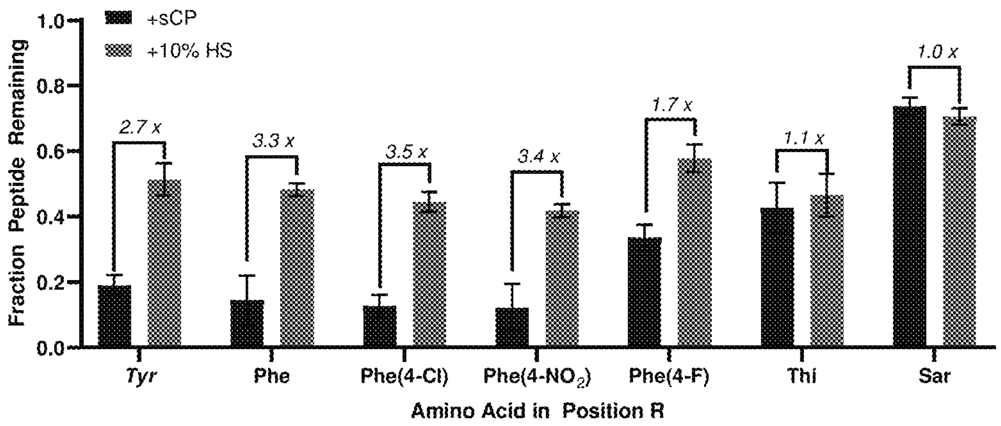
FIG. 5 is a bar graph of the fraction peptide remaining based on amino acid permutation. Select peptides were incubated with 10% human serum and the amount remaining after incubation was detected by an LC/MS assay. Several of those tested showed a preference for cleavage by the 20S CP compared to the serum. However, Thi and Sar showed near equal cleavage by both.

While not wishing to be bound by any specific theory, it is believed that unnatural amino acids, although capable of being cleaved by the protease, are more stable to general proteases contained in human serum to a greater degree than those with only natural amino acids. This is supported by when we first optimized conditions for treating the peptides with human serum using Tyr-containing peptide. We found that using 10% human serum v/v in tris-buffer and incubating with the peptide for 10 min lead to about 50% degradation of the peptide (FIG. 5).

Testing each of the six peptides from the library screen with the same procedure, we found that four of the peptides were cleaved significantly more by the 20S CP compared to when they are incubated in the human serum. Specifically, these were the four Phe derivatives tested. Unfortunately, there was no significant difference in cleavage of the Sar peptide, suggesting the N-methylation did not provide protection from the serum proteases. Overall, the three residues that performed the best, such that there was a greater than three-times favored cleavage by the 20S CP compared to the human serum, were Phe, Phe(4-Cl), and Phe(4-$NO_2$). Because we were interested in the effects of unnatural amino acids in increasing the specificity of our 20S CP recognition sequence, we moved forward with Phe(4-Cl) and Phe(4-$NO_2$) as Tyr substitutes in our probe structure to create TAS2 and TAS3, respectively (FIG. 1B).

TABLE 1

Probes were tested at 30 μM using purified 20S CP. The rate of hydrolysis is the slope of the line created by graphing the fluorescent signal versus time in min. Not surprisingly, TAS1 was turned over the fastest since it has a natural amino acid recognition moiety. However, TAS2 and TAS 3 were also able to be hydrolyzed efficiently.

| Probe | Rate of Hydrolysis (ΔRFU/min) |
|---|---|
| TAS1 | 83.2 |
| TAS2 | 63.8 |
| TAS3 | 28.1 |

Figure 3:
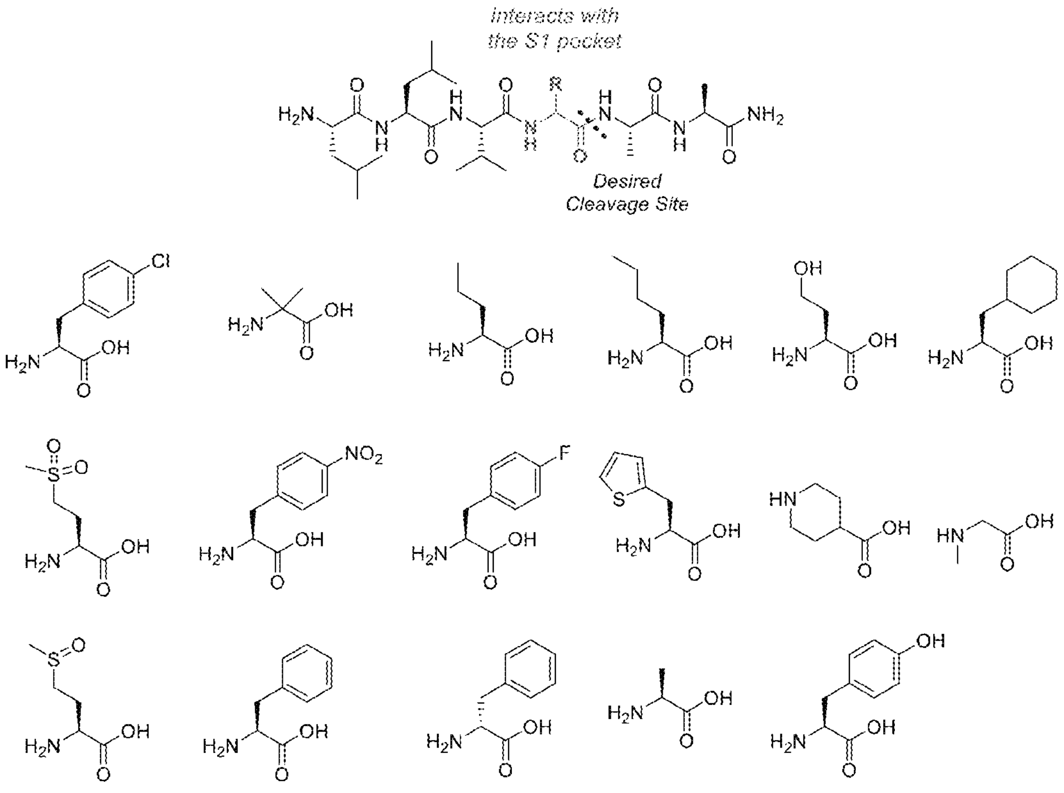
FIG. 3 shows unnatural amino based on the LLVY 20S (SEQ ID NO: 1) CP recognition sequence.

With these new peptide sequences in hand, we returned to incorporating the Rh110-peptoid moiety and to compare the cleavage of TAS1-3 with the 20S CP. We incubated all three probes at various concentrations with 9 nM 20S CP and monitored the change in fluorescence using a microplate reader. From this, we observed that a dose-dependent change in fluorescence was observed for all three probes in triplicate. In order to compare the three probes, we fit a linear regression for the points from 10-60 min for 30 μM of each probe to obtain a rate for the change in fluorescence (Table 1). Of the three, TAS1 was hydrolyzed the quickest, although the slope for TAS2 was similar. Unfortunately, TAS3 had a considerably higher level of background, which is a result of the properties of the 4-nitrophenylalanine. To confirm that the change in fluorescence was due to amide bond cleavage at the expected site on the peptide, we analyzed the samples at a concentration of 30 μM by LC/MS (FIG. 3).

As had been observed with TAS1, both TAS2 and TAS3 only produced the expected cleavage products.

While not wishing to be bound by any specific theory, it is believed that the incorporation of the unnatural amino acids would provide protection for the fluorescent probes from serum proteases compared to the natural Tyr analogue, based on our previous serum stability results. In order to investigate this, we treated the probes with the same conditions as previously, incubating for 10 min and then analyzing by LC/MS how much of the whole probe remained intact. When initially incubating for only 10 min with TAS1, we saw no formation of new peaks in the TIC trace indicating that an increase in stability can also be attributed to incorporating the Rh-110-peptoid moiety. For this reason, we chose to look at how the degradation changed over time. Each probe was incubated with 10% v/v human serum in tris buffer for 0, 30 and 60 min, and then analyzed by LC/MS. After 30 min, a new peak formed for each of the probes with a second new peak appearing after 60 min. Interestingly, neither of these peaks corresponded to the expected cleavage products, such that the serum proteases were not cleaving between the Phe-derivatives and the Rh110. Instead, the first new peak that appeared corresponded to a removal of the A-terminal Leu while the second peak corresponds to the removal of the N-terminal Leu-Leu dipeptide. This would suggest that cleavage caused by the serum proteases would not lead to a fluorogenic signal and that, instead of the unnatural residues protecting the probes from non-specific cleavage, it is the overall structure of the probes that would provide this stability.

We next sought to determine if the TAS probes would be suitable for cell-based assays. To accomplish this, A549 cells were plated at a density of 5,000 cells/well in a black 96 well plate with a black bottom. After allowing the cells to adhere to the plate, the samples were washed with PBS three times then dosed with 10 μM of each probe in modified KRBH buffer. The change in fluorescence was recorded on a microplate reader for 90 min. After allowing the signal to equilibrate for 25 mm, each sample was set to zero and the future time points were scaled accordingly. As was done with the biochemical data, a linear regression was fit to each set of data. From the slope, it is observed that the rate for TAS2 was the highest. To determine the in-cell selectivity, a set of samples pretreated with MG-132 (10 μM), a proteasome inhibitor, was included for each probe. These samples were pre-incubated with MG-132 in cell culture media for one hour before washing with PBS and dosing with each probe in modified KRBH buffer. After plotting the average value over time and performing a linear regression, it was observed that the slope for each probe was decreased by about 50% or greater when cells were incubated with MG-131 Plotting the average of each sample at their end point showed all probes had a significantly decreased signal when pretreated with MG-132 (FIG. 6), supporting the expected selectivity of the probes for the 20S CP over other proteases. To ensure this decrease was not a consequence of cell death, cells were treated in the same way and analyzed using Cell-Titer Glo.

Figure 7:
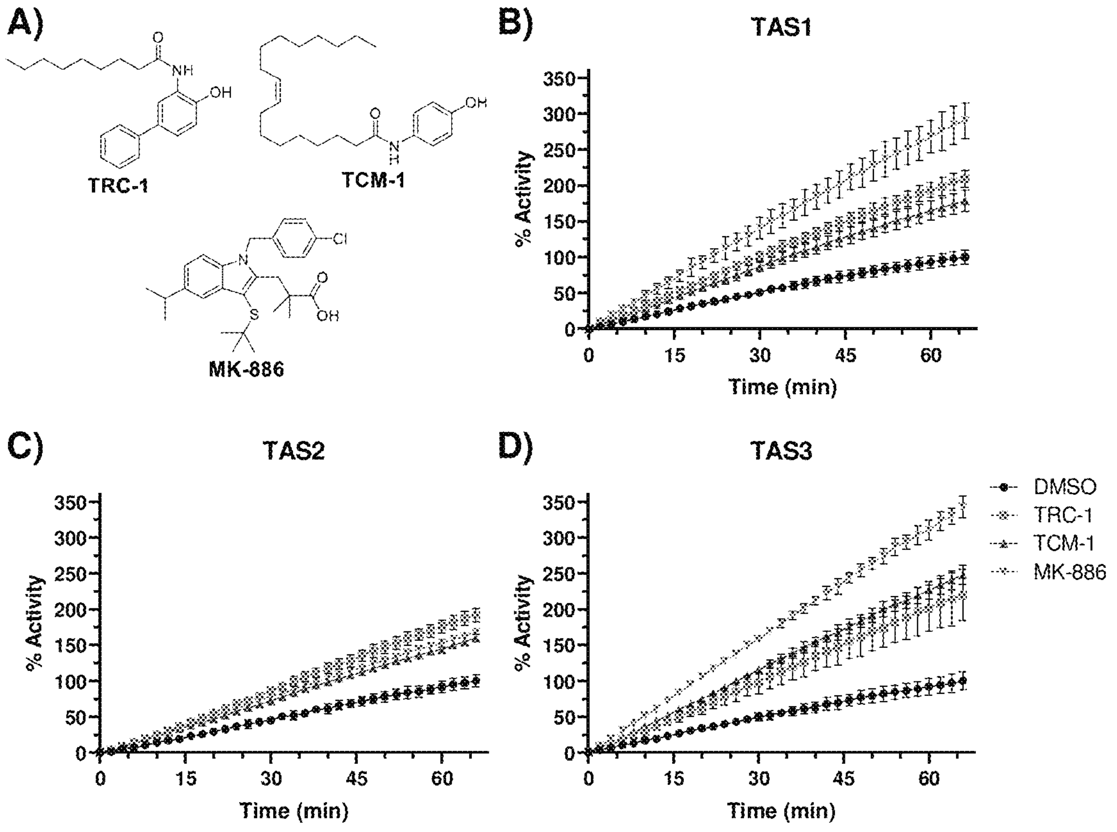
FIG. 7A depicts three small molecule stimulators previous validated using other proteasome stimulation assays.
FIG. 7B-7D show the analysis of TAS probes (TAS-1-B, TAS-2-C, TAS-3-D) for their ability to detect different small molecule stimulators using human purified 20S proteasome.

In addition to determining if our probes are capable of detecting a decrease in proteasome activity, we were also interested in monitoring molecules which have shown to increase proteasome activity, also known as proteasome stimulators. Various stimulators (FIG. 7A) have been shown to be effective in cells by analyzing changes in GTP-fusion protein degradation. However, this method requires transfection of the MT-fusion protein into cells and analysis by Western blot. Given the promising results with MG-132, we expected our probes to be sensitive enough to detect proteasome stimulation in a similar manner. Using three molecules reported to have various degrees of stimulation, cells were dosed for one hour before washing and adding in each probe. The samples were then monitored for changes in fluorescence and analyzed in the same way as the MG-132 experiment.

With using all three probes, the stimulator molecules showed an increase in rate of cleavage compared to DMSO treated samples. For TAS1 and TAS3, this percent increase was found to be dependent on the molecule used, suggesting that either would be effective in future studies and could be used to determine the effects of a variety of stimulating molecules. This result is exciting because either of these new probes can be used directly in cells to monitor the real time increase in proteasome activity. Previously proteasome stimulators had been discovered using a biochemical assay that required purified proteasome. As with all enzyme purifications, the batch to batch activity can vary greatly, leading to inconsistent results. Our probes can be used in a variety of cell lines and in combination with other activity-based probes or cell markers.

Proteasome inhibitors approved by the FDA, such as bortezomib and carfilzomib, are effective in hematological cancers, including multiple myeloma, due to these cells' strong dependency on proteasome activity to survive. Although a common way to determine a cell's dependency on proteasome activity is by treating cells with a proteasome inhibitor and observing its toxicity, we sought to instead use TAS2 as a way to examine the relative proteasome activity levels in different cell lines; these include MM.1R, A498, SK-MEL-2, MEL-92.1, SH-SY5Y and HEK293T cell lines. TAS2 was chosen as it was shown to produce the highest signal in the A549 cell lines, FIG. 6.

TABLE 2

Six different cancer cell lines were incubated with TAS2 for 60 min. The amount of proteasome activity variedly greatly indicating how much proteasome each of these cancer cell lines require to survive.

| Cell Line | Rate of Hydrolysis (ΔRFU/min) |
|---|---|
| MM.1R | 81.6 ± 25.5 |
| A498 | 39.6 ± 4.8 |
| MEL-92.1 | 16.4 ± 2.6 |
| SK-MEL-2 | 12.1 ± 1.3 |
| HEK-293T | 6.7 ± 3.2 |
| SH-SY5Y | 5.8 ± 0.4 |

To compare these cells lines, each was plated at the same density of 5,000 cells/well in a black 96 well plate—for adherent cells lines A498, SK-MEL-2, MEL-92.1, SH-SY5Y and HEK293T, the cells were allowed to adhere overnight before using in the assay; MM.1R cells were plated and used directly after. Samples were incubated with either DMSO or TAS2 (10 μM) for 15 min, washed with PBS three times before putting the plate in a microplate reader to record the fluorescence intensity over 90 min. The experiment was performed in technical triplicate and experimental duplicate for each cell line and the rate of hydrolysis of TAS-2 was determined, Table 2.

A wide range of slopes were observed for the various cells lines. This suggests that there are different levels of proteasome activity associated with the cells lines tested. The values observed may suggest a trend between slope for TAS2 and sensitivity of each cell line to proteasome inhibitors. For example, with the greatest slope, MM.1R is known to be strongly dependent on proteasome activity and proteasome inhibition has been found to be a very effective treatment strategy for multiple myeloma. On the other hand, HEK293T, a model non-cancerous cell line, is not expected to have a high degree of proteasome activity, and has one of the lowest slopes with TAS2. We believe the variability of the MM.1R cell line is because some cells are lost during the wash protocol since they are non-adherent. However, they still possess the highest amount of proteasome activity, which was expected.

We also sought to correlate this proteasome activity trend with susceptibility to a proteasome inhibitor by determining the $IC_{50}$ values of MG-132 with these six cells. Cells were dosed for 48 hours with increase concentrations of MG-132 then analyzed using Cell-Titer Glo to determine cell viability. MG-132 was most toxic to MM.1.R, with an $IC_{50}$ of 264 nM. The $IC_{50}$'s for the remaining cell lines were found to be higher than that of MM.1R, they did not follow the same trend as proteasome activity observed using TAS2. Considering this, we still believe comparing cell lines for proteasome activity based on fluorescence with TAS2 would still provide insight to the relative dependency of various cancer cell lines on proteasome activity.

CONCLUSIONS in this example, we describe the development of a new set of activity-based probes for the proteasome. Our first probe, named TAS1, showed improved sensitivity compared to the commercially available Suc-LLVY-AMC (SEQ ID NO: 1; FIG. 1C), which was a result of only the desired cleavage of the bond between Rh110 and Tyr residue (FIG. 2). With the goal of improving the selectivity TAS1 towards the proteasome over other cellular proteases, we screened a small peptide library, incorporating unnatural amino acids in place of Tyr (FIG. 3). By incubating each peptide with purified 20S CP and analyzing the samples by LC/MS, we found several which had greater cleavage rates compared to Tyr. From these results, we selected six of the most promising peptides to evaluate their serum stability (FIG. 5). Comparing these two sets of data, we found that the peptides containing Phe(4-Cl) (TAS2) and Phe(4-$NO_2$) (TAS3) showed a greater preference for proteasome-mediated cleavage as compared to Tyr-containing peptide, suggesting incorporating them would produce improved probes as well.

Figure 6:
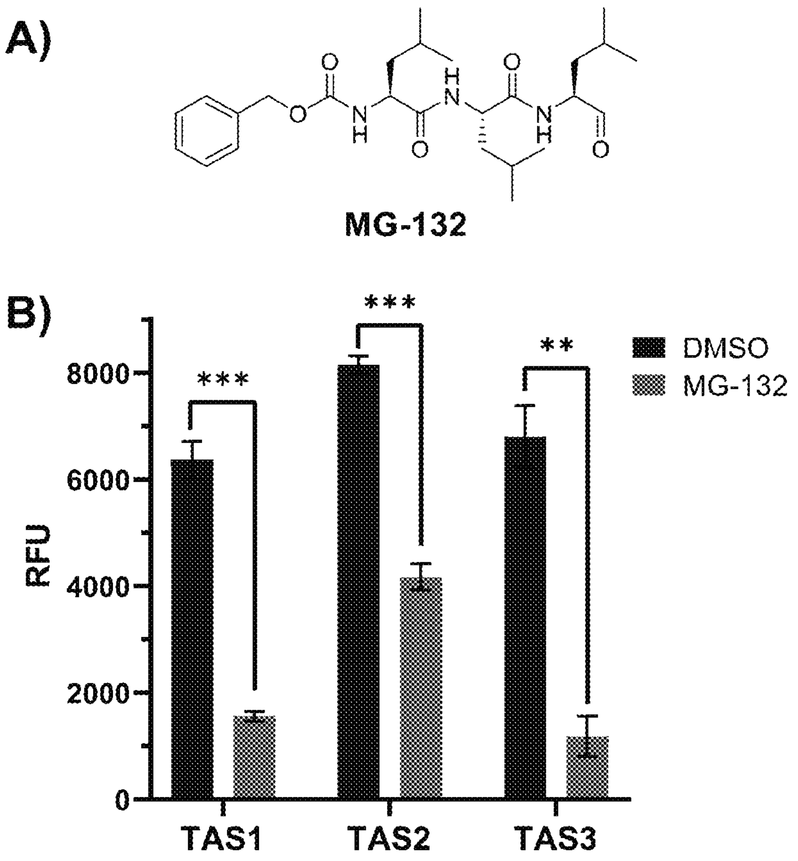
FIG. 6A is the structure of proteasome inhibitor MG-132.
FIG. 6B is a bar graph of the selectivity for the proteasome with TAS1-3. All three probes were incubated with A549 cells. By pre-incubating with MG-132, the signal can be significantly reduced when using all three probes indicating that the majority of probe cleavage is through interacting with the proteasome.

After synthesizing TAS2 and TAS3, we compared the protease selectivity of all three probes by analyzing the products produced after incubating with human serum by LC/MS (FIG. 6). Excitingly, all three probes showed no productive cleavage, that is no cleavage that would produce an increase in fluorescence, when incubated in the presence of human serum for either 30 or 60 min. As such, we concluded that it was the general probe structure, including the Rh110 and peptoid regions, which prevented cleavage of TAS1-3 by the proteases found in human serum.

By using live cells, we have been able to demonstrate that selectivity for the proteasome is maintained when using TAS1-3 in a plate reader-based fluorescence assay (FIG. 6). For all three probes, a significant decrease in signal is observed when comparing cells with and without incubating in the presence of the proteasome inhibitor, MG-132; since MG-132 was used at 50% its reported $IC_{50}$ in A549 cells, it was not expected that the fluorescence be completely eliminated. Performing a screening assay in cells rather than with purified proteasome also allows the evaluation of the cell-permeability of the inhibitor, eliminating the need to follow-up with primary hits that then are only demonstrated to work in the biochemical assay. Sensitivity of our probes also allows for the detection of weak inhibitors, whose scaffolds previously have not been considered as potential proteasome inhibitors.

Using three different stimulating small molecules previously validated using other methods, we found both TAS1 and TAS3 would be suitable to use in such an assay. Specifically, TAS1 and TAS3 show greater than 3-fold increase in activity when comparing cells treated with MK-886 treated to those treated with DMSO. Also, a difference in stimulation amount for the three small molecules tested was also observed, suggesting that a wide-range of proteasome stimulators can be evaluated with our probes. An increase in proteasome activity can be detected after as little as 15 min of incubation time, which can help to increase throughput during a screening campaign. Furthermore, either TAS1 or TAS3 can be used in combination with other cellular tools, including cell cycle markers, or to correlate proteasome activity with MHC-I expression levels. This is a very important characteristic of TAS1 and TAS3 as there are a number of important questions regarding the cellular impact of increasing proteasome activity or restoring activity in diseased cells where proteasome activity is decreased.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

It will be understood by one of ordinary skill in the relevant arts that other suitable modifications and adaptations to the compositions and methods described herein are readily apparent from the description of the disclosure contained herein in view of information known to the ordinarily skilled artisan, and may be made without departing from the scope of the disclosure. Having now described the present disclosure in detail, the same will be more clearly understood by reference to the following examples, which are included herewith for purposes of illustration only and are not intended to be limiting of the disclosure.

What is claimed is:

1. A compound of formula (I):

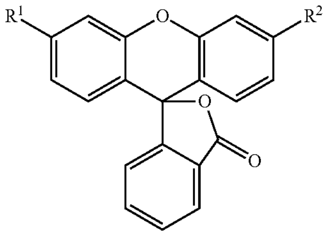

wherein:

R is $A_1$-$A_2$-$A_3$-$A_4$* (SEQ ID NO: 2) or $A_1$-$A_2$-$A_3$-$A_4$-$A_5$* (SEQ ID NO: 2);

$R^2$ is:

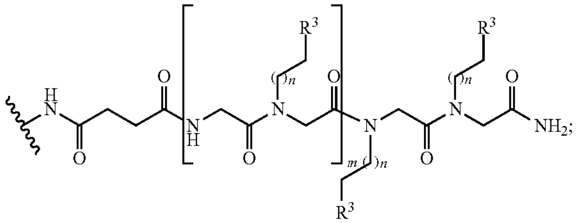

each $R^3$ is independently —$N(CH_3)_2$ or —$OCH_3$;

$A_1$ is Leu or Ac;

$A_2$ is Leu, Gly, or Arg;

$A_3$ is Val, Pro, or Leu;

$A_4$ is Tyr, Leu, or Arg;

$A_5$ is Asp;

each instance of n is independently 1, 2, or 3; and m is 1, 2, or 3.

2. The compound of claim 1, wherein at least one instance of $R^3$ is $N(CH_3)_2$.

3. The compound of claim 1, wherein all instances of $R^3$ are —$N(CH_3)_2$.

4. The compound of claim 1, wherein at least one instance of $R^3$ is —$OCH_3$.

5. The compound of claim 1, wherein all instances of $R^3$ are —$OCH_3$.

6. The compound of claim 1, wherein $R^2$ is
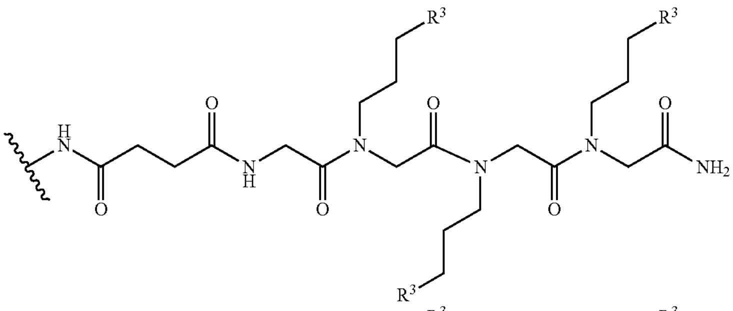
or
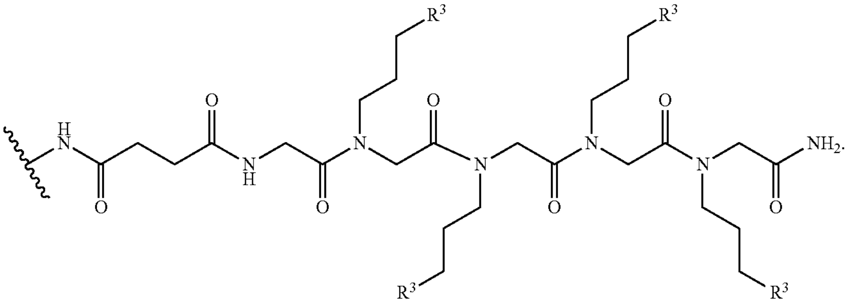
7. The compound of claim 1, wherein the compound is selected from the group consisting of:
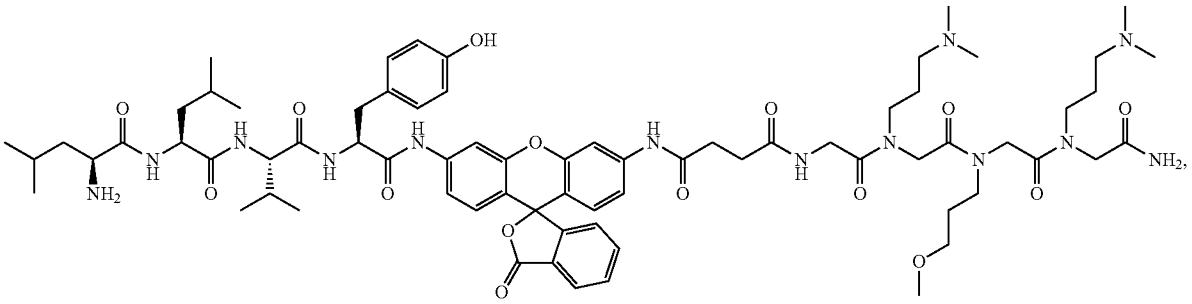
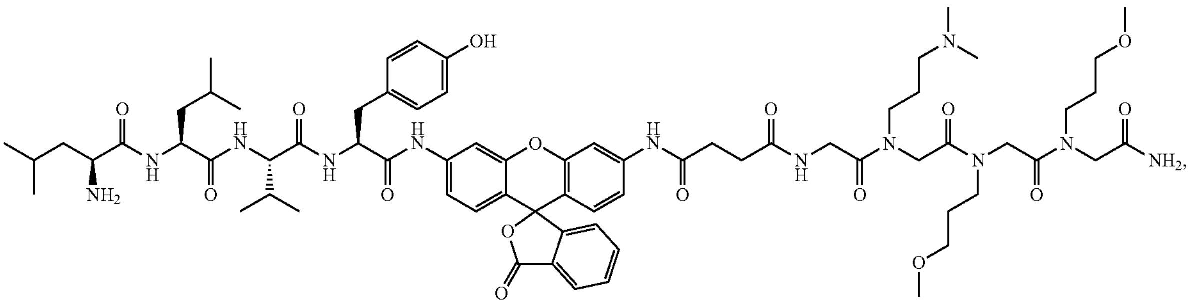
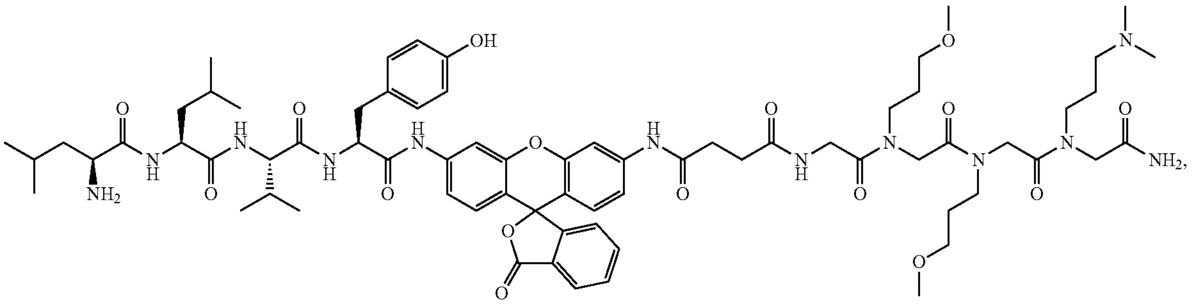

-continued
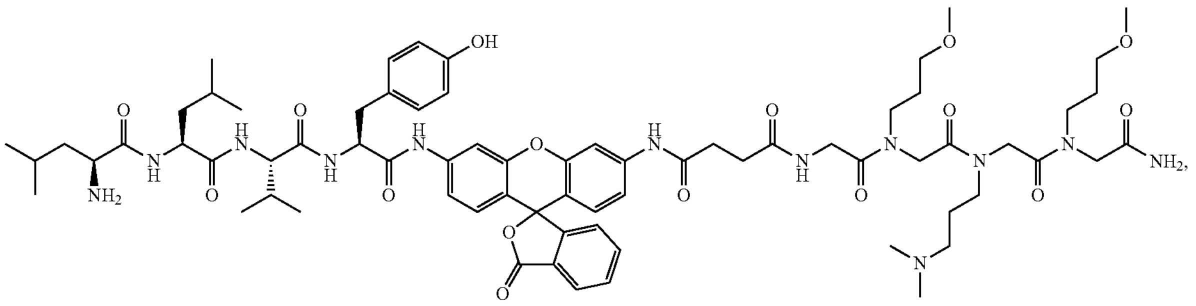
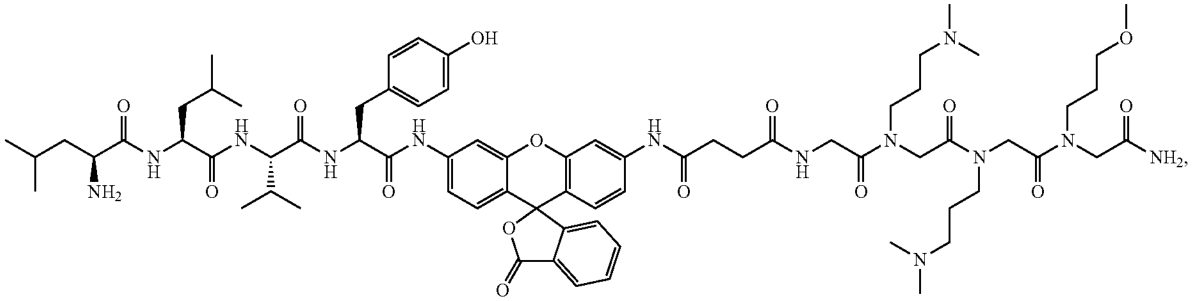
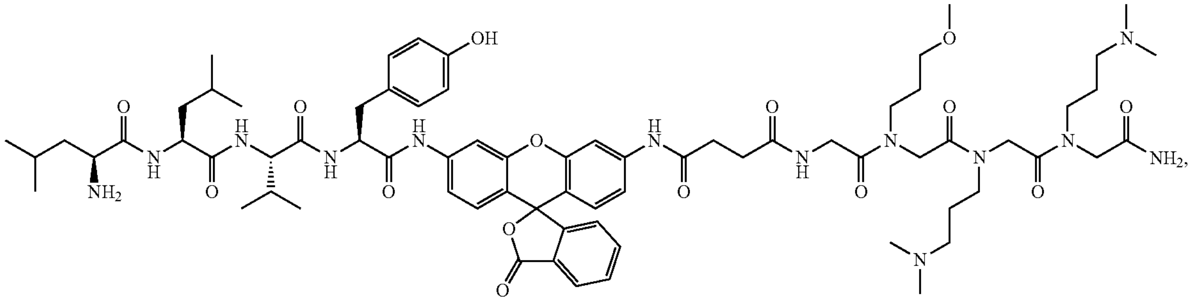
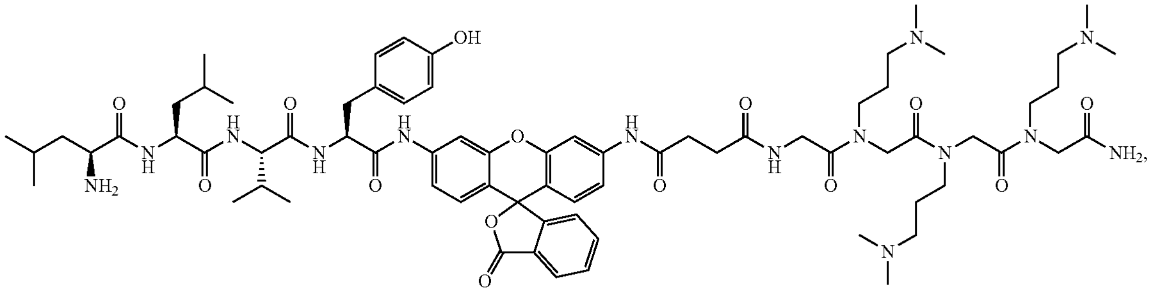
and
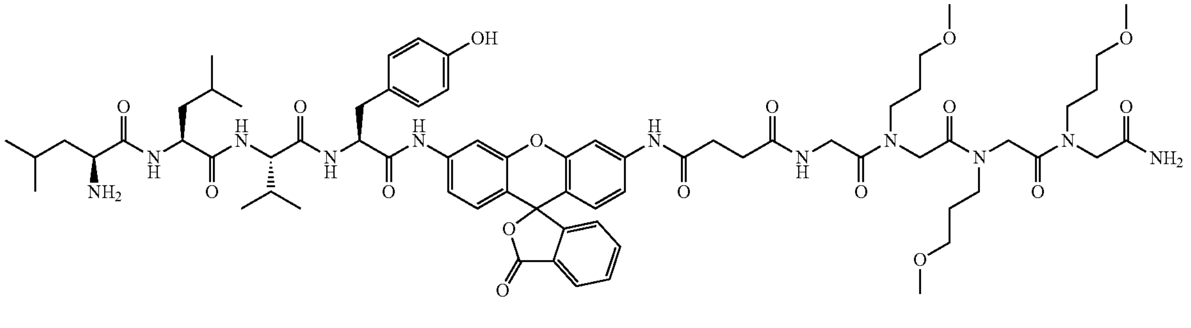

or selected from the group consisting of:
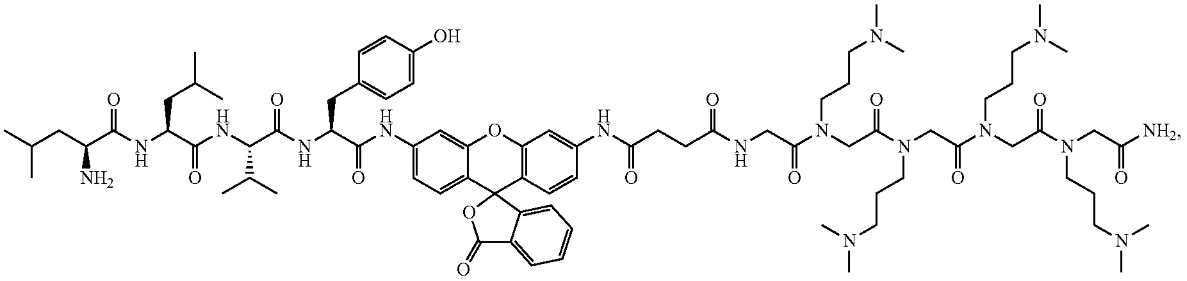
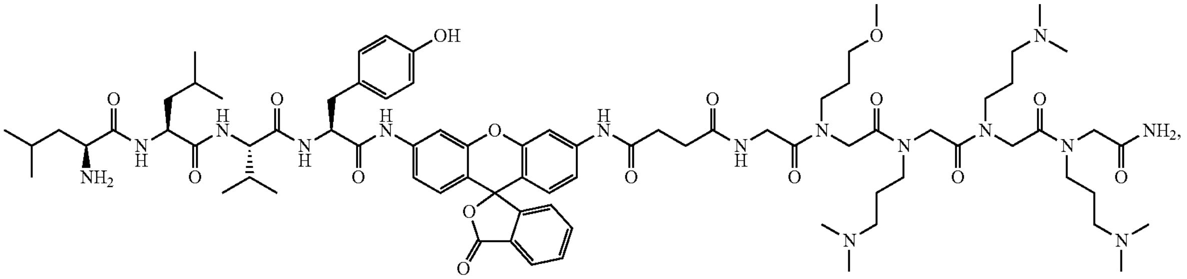
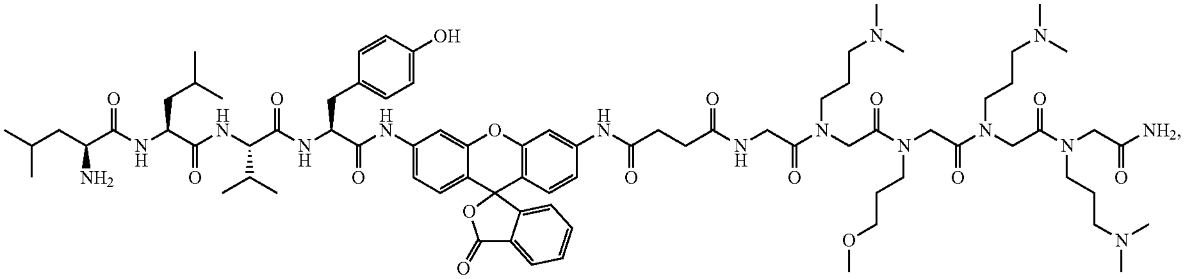
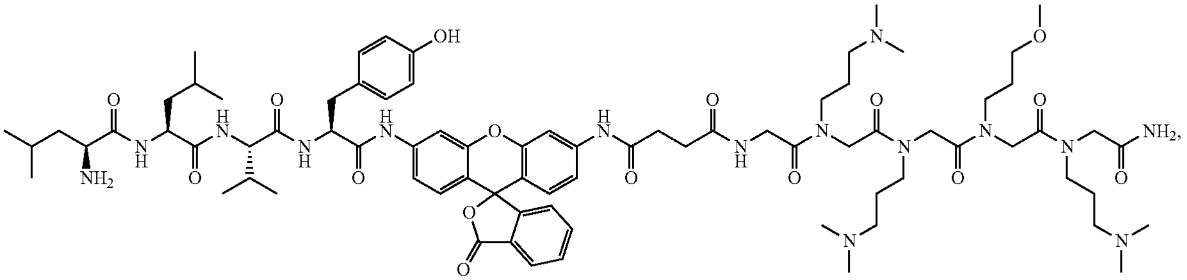
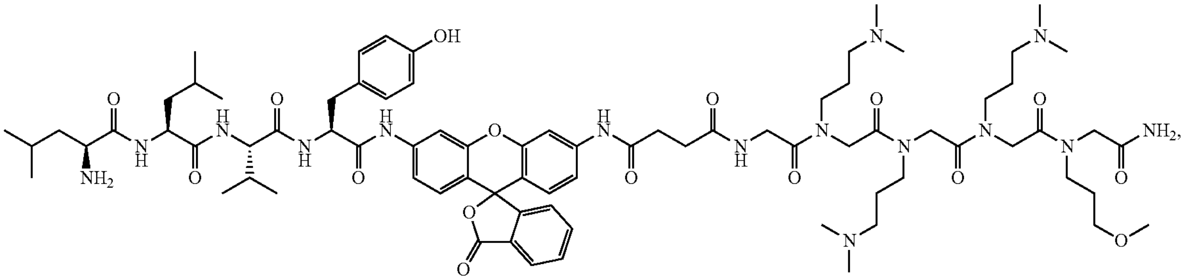
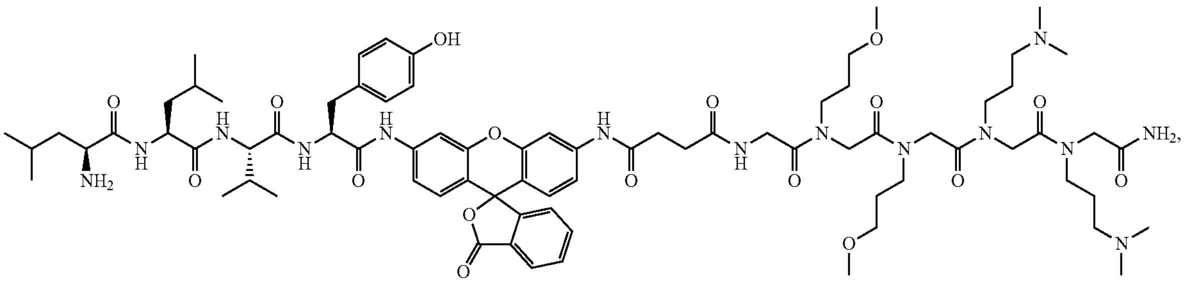

-continued
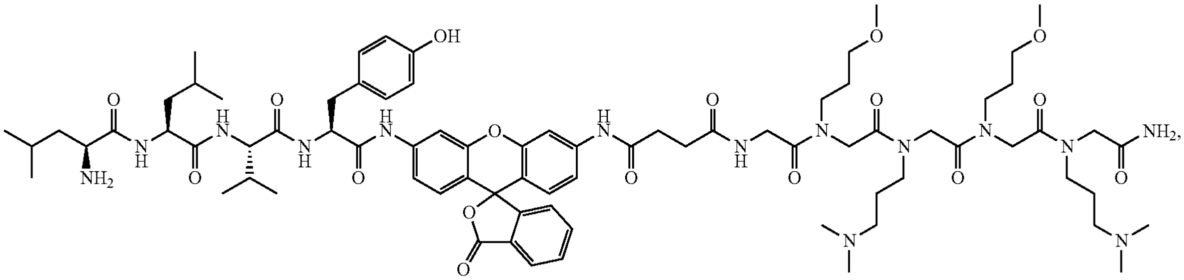
,
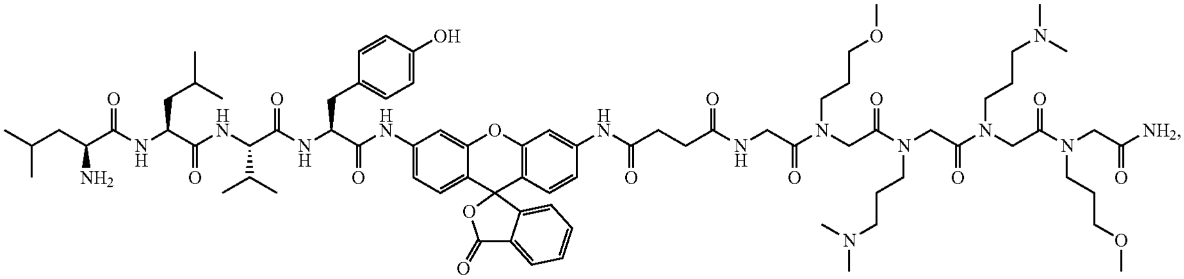
,
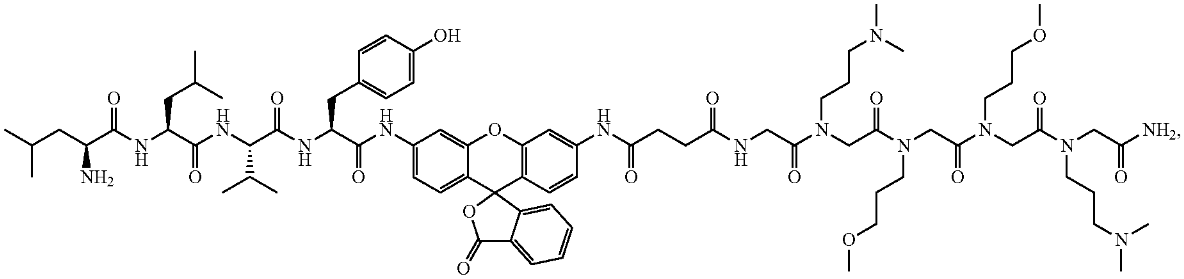
,
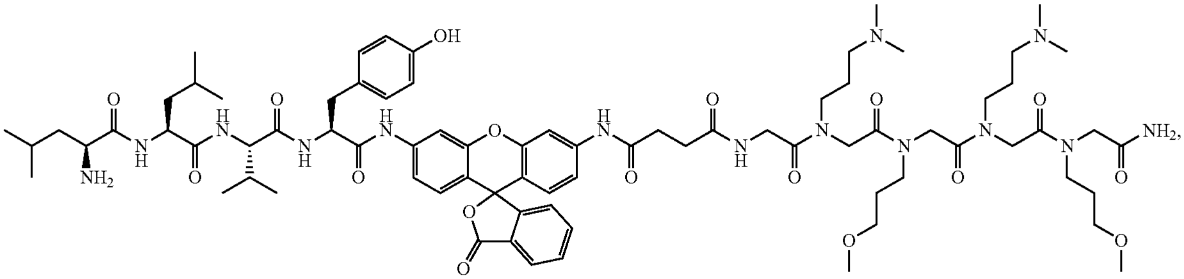
,
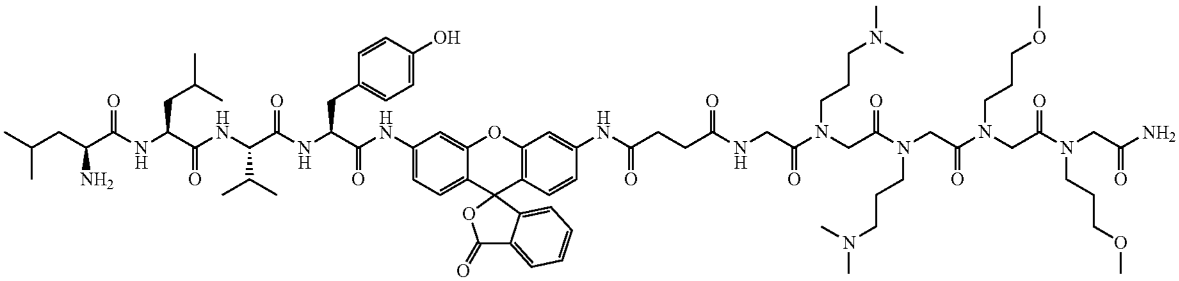
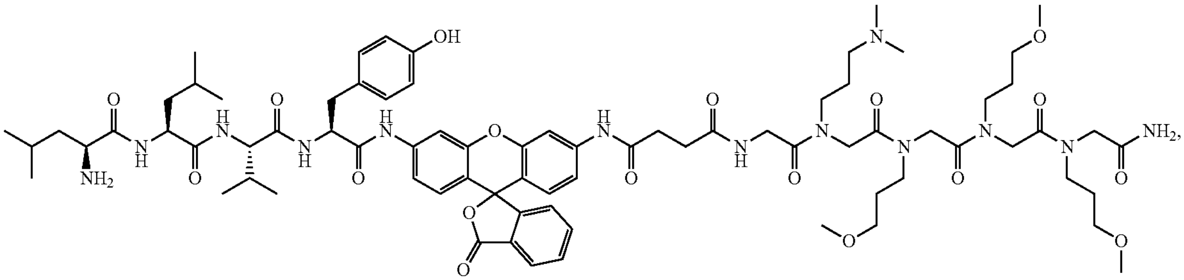
, -continued
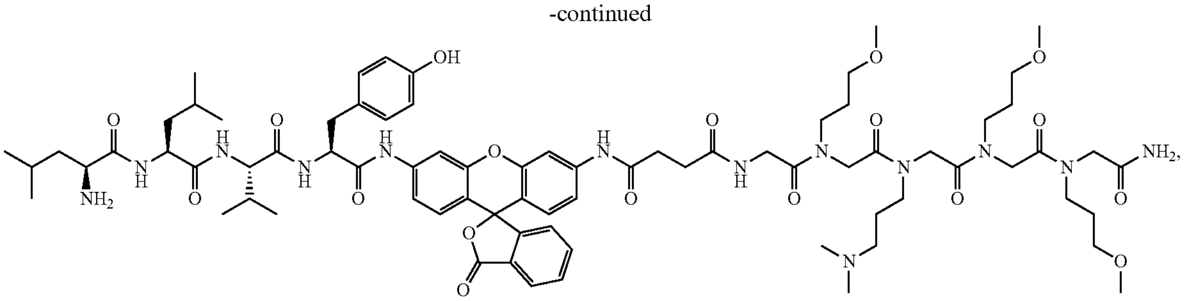
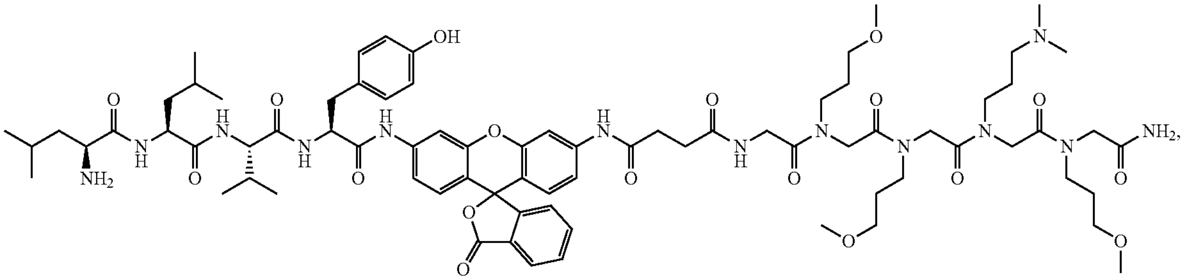
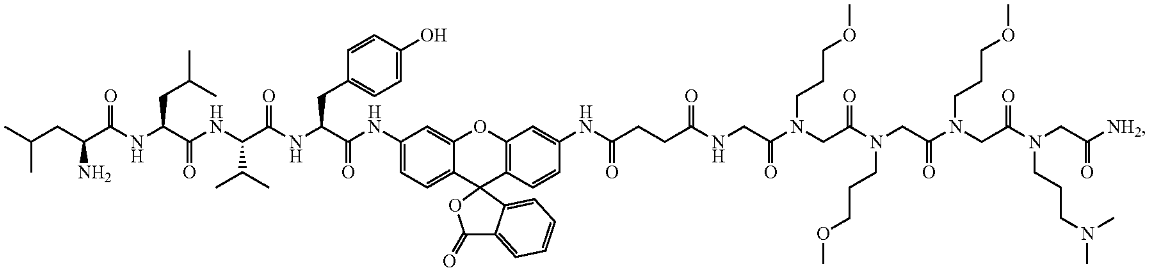
and
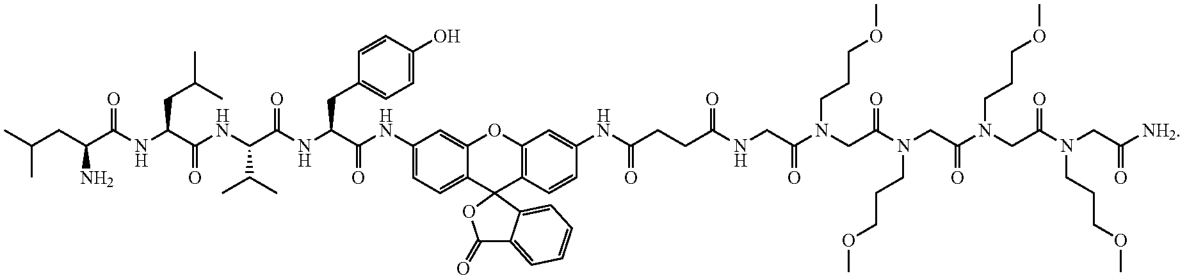 [SMILES: COCCCN(CC(N)=O)C(=O)CN(CCCOC)C(=O)CN(CCCOC)C(=O)CN(CCCOC)C(=O)CNC(=O)CCC(=O)Nc1ccc2c(c1)Oc1cc(NC(=O)[C@H](Cc3ccc(O)cc3)NC(=O)[C@@H](NC(=O)[C@H](CC(C)C)NC(=O)[C@@H](N)CC(C)C)C(C)C)ccc1C21OC(=O)c2ccccc21]
8. The compound of claim 1, wherein the compound is:
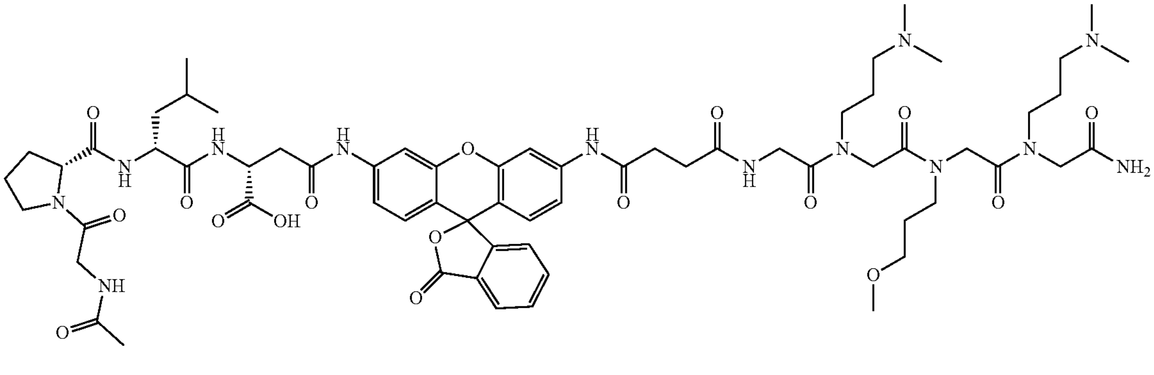
or -continued

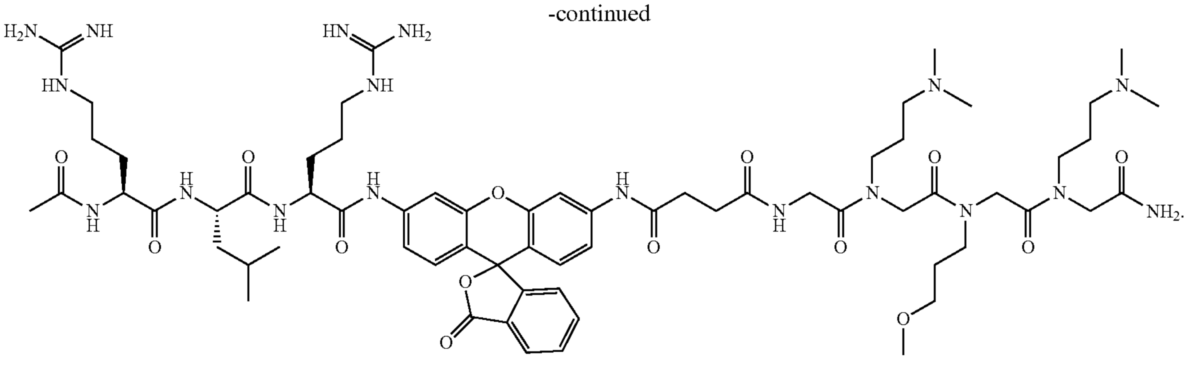

9. A method of monitoring a real time increase in proteasome activity in cells, the method comprising contacting the cells with a compound of formula (I)

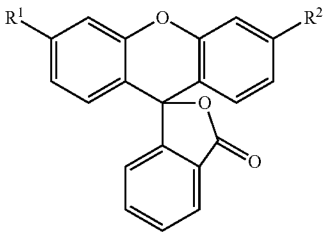

wherein:
$R^1$ is $A_1$-$A_2$-$A_3$-$A_4$* (SEQ ID NO: 2) or $A_1$-$A_2$-$A_3$-$A_4$-$A_5$-* (SEQ ID NO: 2);
$R^2$ is:

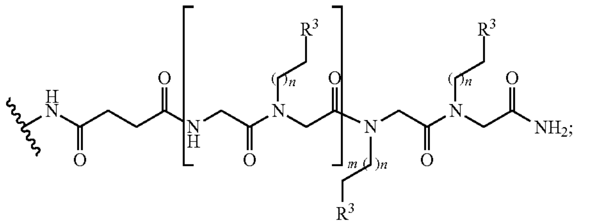

each $R^3$ is independently —$N(CH_3)_2$ or —$OCH_3$;
$A_1$ is Leu or Ac;
$A_2$ is Leu, Gly, or Arg;
$A_3$ is Val, Pro, or Leu;
$A_4$ is Tyr, Leu, or Arg;
$A_5$ is Asp;
each instance of n is independently 1 2, 3; and
m is 1, 2, 3,
and measuring proteasome activity by the accumulation of a fluorescent signal.

10. The method of claim 9, wherein the cells are cells from different cancer cell lines and the relative of levels of proteasome activities between the different cancer cell lines are differentiated.

11. The method of claim 10, wherein the method further comprises contacting the cells with small molecule stimulators and monitoring the effects of small molecule stimulators on the relative levels of proteasome activities between the different cancer cell lines.

12. The method of claim 10, wherein the method further comprises contacting the cells with small molecule inhibitors and small molecules stimulators of the proteasome and evaluating the small molecule inhibitors and the small molecule stimulators on the relative levels of proteasome activities between the different cancer cell lines.

13. A method of determining the threshold of proteasome activity required for a cancer cell type to be highly susceptible to proteasome inhibitors, the method comprising contacting the cells with a compound of formula (I)

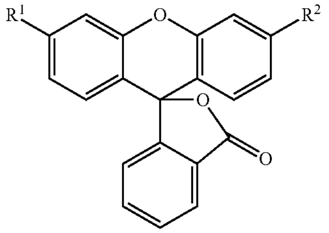

wherein:
$R^1$ is $A_1$-$A_2$-$A_3$-$A_4$* (SEQ ID NO: 2) or $A_1$-$A_2$-$A_3$-$A_4$-$A_5$-* (SEQ ID NO: 2);
$R^2$ is:

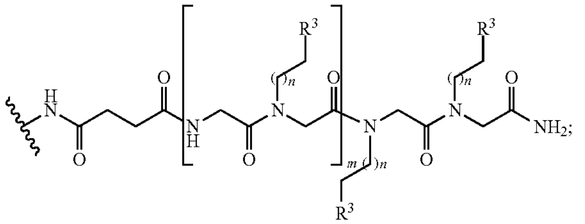

each $R^3$ is independently —$N(CH_3)_2$ or —$OCH_3$;
$A_1$ is Leu or Ac;
$A_2$ is Leu, Gly, or Arg;
$A_3$ is Val, Pro, or Leu;
$A_4$ is Tyr, Leu, or Arg;
$A_5$ is Asp;
each instance of n is independently 1 2, 3; and
m is 1, 2, 3,
and measuring proteasome activity by the accumulation of a fluorescent signal.

* * * * *

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: A synthetic sequence

<400> SEQUENCE: 1

Leu Leu Val Tyr
1

<210> SEQ ID NO 2
<211> LENGTH: 5
<212> TYPE: PRT
<213> ORGANISM: Artificial Sequence
<220> FEATURE:
<223> OTHER INFORMATION: A synthetic sequence
<221> NAME/KEY: SITE
<222> LOCATION: 1
<223> OTHER INFORMATION: Xaa = Leu or Ac
<221> NAME/KEY: SITE
<222> LOCATION: 2
<223> OTHER INFORMATION: Xaa = Leu, Gly, or Arg
<221> NAME/KEY: SITE
<222> LOCATION: 3
<223> OTHER INFORMATION: Xaa = Val, Pro, or Leu
<221> NAME/KEY: SITE
<222> LOCATION: 4
<223> OTHER INFORMATION: Xaa = Tyr, Leu, or Arg
<221> NAME/KEY: SITE
<222> LOCATION: 5
<223> OTHER INFORMATION: Xaa = absent or Asp

<400> SEQUENCE: 2

Xaa Xaa Xaa Xaa Xaa
1               5